(12) United States Patent
Usman et al.

(10) Patent No.: US 11,305,256 B2
(45) Date of Patent: Apr. 19, 2022

(54) HYBRID ZEOLITIC IMIDAZOLATE FRAMEWORK AND A METHOD OF CAPTURING CARBON DIOXIDE

(71) Applicant: King Fahd University of Petroleum and Minerals, Dhahran (SA)

(72) Inventors: Muhammad Usman, Dhahran (SA); Bassem A. Al-Maythalony, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 348 days.

(21) Appl. No.: 16/720,535

(22) Filed: Dec. 19, 2019

(65) Prior Publication Data
US 2021/0187475 A1 Jun. 24, 2021

(51) Int. Cl.
*B01D 53/04* (2006.01)
*B01J 20/22* (2006.01)
(Continued)

(52) U.S. Cl.
CPC ............ *B01J 20/226* (2013.01); *B01D 53/04* (2013.01); *B01J 20/28059* (2013.01);
(Continued)

(58) Field of Classification Search
CPC .. B01D 53/02; B01D 53/04; B01D 2253/108; B01D 2253/202; B01D 2253/204;
(Continued)

(56) References Cited

U.S. PATENT DOCUMENTS 9,512,145 B2 12/2016 Yaghi et al.
2009/0214407 A1* 8/2009 Reyes .................... B01J 20/226
423/230
(Continued)

FOREIGN PATENT DOCUMENTS

CN 106317086 B 9/2018

OTHER PUBLICATIONS

Yaghi ; Metal-organic and zeolitic imidazolate frameworks (MOFs and ZIFs) for highly selective separations ; Feb. 1, 2008 to Jan. 31, 2012 ; US Department of Energy ; 15 Pages.
(Continued)

*Primary Examiner* — Frank M Lawrence, Jr.
(74) *Attorney, Agent, or Firm* — Oblon, McClelland, Maier & Neustadt, L.L.P.

(57) ABSTRACT

A hybrid zeolitic imidazolate framework having an isolated purity of at least 95 wt. %, which is a coordination product formed between zinc(II) ions, a linker of formula (I), and a linker of formula (II);

(Continued)

wherein each linker of formulae (I) and (II) links together adjacent zinc(II) ions, $R^1$ and $R^2$ are independently a hydrogen, an optionally substituted alkyl, an optionally substituted aryl, a halo, a nitro, or a cyano, and $R^3$ and $R^4$ are independently hydrogen, an optionally substituted alkyl, an optionally substituted aryl, or an optionally substituted arylalkyl. A method of making the hybrid zeolitic imidazolate framework and a method of capturing $CO_2$ from a gas mixture with the hybrid zeolitic imidazolate framework.

20 Claims, 22 Drawing Sheets

(51) Int. Cl.
    *B01J 20/28* (2006.01)
    *C07D 233/64* (2006.01)
    *B01J 20/30* (2006.01)

(52) U.S. Cl.
    CPC ... *B01J 20/28061* (2013.01); *B01J 20/28064* (2013.01); *B01J 20/28071* (2013.01); *B01J 20/3085* (2013.01); *C07D 233/64* (2013.01); *B01D 2253/204* (2013.01); *B01D 2253/306* (2013.01); *B01D 2253/311* (2013.01); *B01D 2257/504* (2013.01)

(58) Field of Classification Search
    CPC ........ B01D 2253/306; B01D 2253/311; B01D 2257/504; Y02P 20/151; B01J 20/226; B01J 20/28059; B01J 20/28061; B01J 20/28064; B01J 20/28071; B01J 20/3085; C07D 233/64; Y02C 20/40
    See application file for complete search history.

(56) References Cited

U.S. PATENT DOCUMENTS

| | | |
|---|---|---|
| 2010/0186588 A1* | 7/2010 | Yaghi ................. B01D 19/00 95/127 |
| 2013/0197235 A1 | 8/2013 | Thompson et al. |
| 2017/0252720 A1* | 9/2017 | Odeh ..................... C08K 5/56 |
| 2018/0326397 A1* | 11/2018 | Yaghi ..................... C01B 39/00 |
| 2019/0282997 A1* | 9/2019 | Falkowski ............. B01J 20/226 |

OTHER PUBLICATIONS

Cacho-Bailo, et al. ; Sequential amine functionalization inducing structural transition in an aldehyde-containing zeolitic imidazolate framework: application to gas separation membranes† ; CrystEngComm, Issue 11 ; 2017 ; Abstract Only ; 3 Pages.

Thompson, et al. ; Tunable CO Adsorbents by Mixed-Linker Synthesis and Postsynthetic Modi_cation of Zeolitic Imidazolate Frameworks ; J. Phys. Chem. C, 117, 16 ; 2013 ; Abstract Only ; 2 Pages.

\* cited by examiner

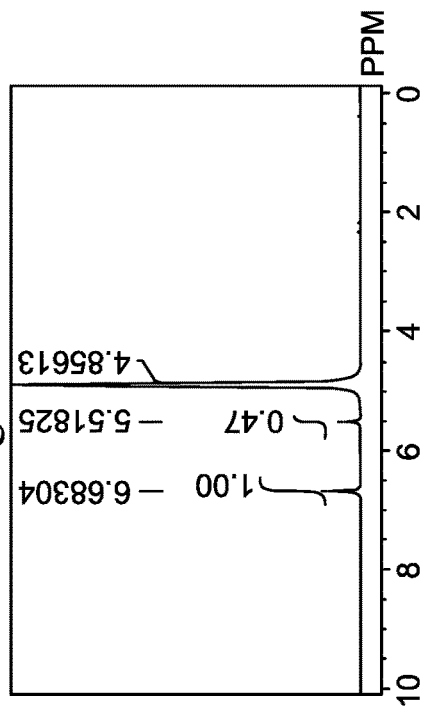
Fig. 5M
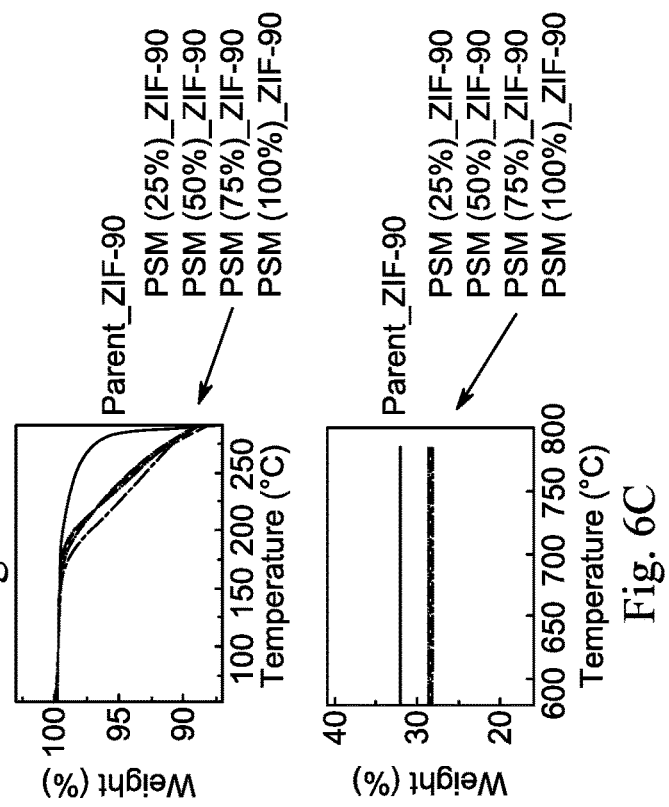
Fig. 6B
Fig. 6C
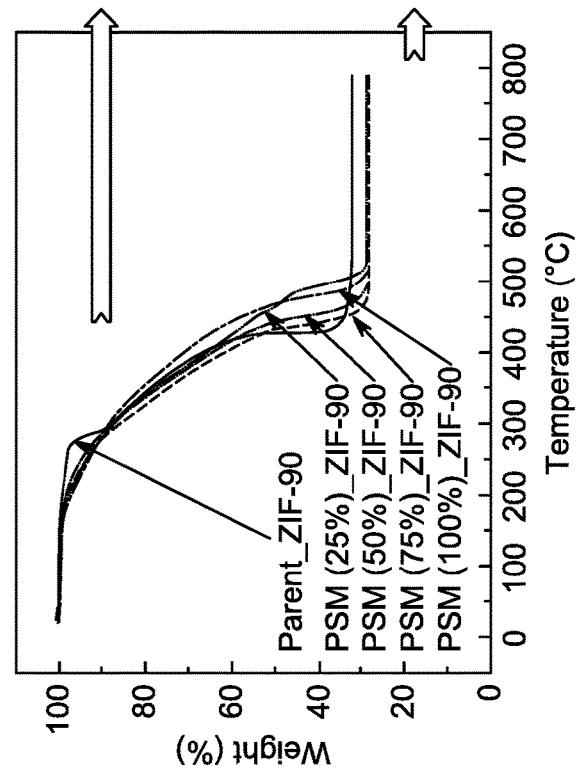
Fig. 6A

HYBRID ZEOLITIC IMIDAZOLATE FRAMEWORK AND A METHOD OF CAPTURING CARBON DIOXIDE

STATEMENT OF ACKNOWLEDGEMENT

Financial support from KFUPM-DSR is gratefully acknowledged under Project No. DF181004.

BACKGROUND OF THE INVENTION

Field of the Invention

The present invention relates to a hybrid zeolitic imidazolate framework (hybrid ZIF), and methods of capturing carbon dioxide ($CO_2$) with the hybrid ZIF.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Carbon dioxide is major contributor to global warming and thus many strategies have been investigated to mitigate $CO_2$ levels and emissions, including research towards various carbon dioxide capture materials. However, materials having high carbon dioxide uptake, selective carbon dioxide capture and low isosteric heat of adsorption are still needed.

Zeolitic imidazolate framework-90 (ZIF-90), a material that possesses a zeolitic structure, has attractive features that make it a suitable candidate for selective gas capture and separation. Namely, ZIF-90 possesses a sodalite topology with a small window size and can be subjected to linker functionalization owing to the aldehyde group attached to the imidazolate linker. ZIF-90 possesses a zeolitic structure with a large pore size of >11 Å that is surrounded by 4- and 6-membered windows with the carboxyaldehyde being located at the 2-position of the imidazolate linker. See W. Morris, C. J. Doonan and O. M. Yaghi, *Inorg Chem*, 2011, 50, 6853-6855, incorporated herein by reference in its entirety. The 6-membered window is the only accessible window, which is ~4 Å in diameter. The ability to modify the aldehyde of the imidazole moiety allows for gas transport modulation through the 6-membered ring.

ZIF-90 (FIG. 2, the structure in the middle) possess a high potential for functionalization that can lead to different materials of entirely different porosity depending on the utilized alkylamine (FIG. 2, the structures in the corners) by reducing the pore size of parent ZIF-90s 6-membered window owing to the orientation of the alkyl group over the window. See P. Á. Szilágyi, P. Serra-Crespo, J. Gascon, H. Geerlings and B. Dam, *Frontiers in Energy Research*, 2016, 4, 9, incorporated herein by reference in its entirety. Several examples found in literature demonstrate the use of ZIF-90 and post-synthetically modified ZIF-90 (PSM-ZIF-90) in membranes, pure ZIF-90 membranes on alumina support with ethanolamine functionalization for $H_2/CH_4$ separation, and ZIF-90 coating layers on hollow fiber membranes with gaseous molecular sieving properties. See A. Huang, W. Dou and J. Caro, *Journal of the American Chemical Society*, 2010, 132, 15562-15564; A. Huang and J. Caro, *Angewandte Chemie International Edition*, 2011, 50, 4979-4982; and A. J. Brown, J. Johnson, M. E. Lydon, W. J. Koros, C. W. Jones and S. Nair, *Angewandte Chemie International Edition*, 2012, 51, 10615-10618, each incorporated herein by reference in their entirety. ZIF-90 hydrophobicity has also been adjusted by PSM with pentafluoro aniline for oil separation. See C. Liu and A. Huang, *New Journal of Chemistry*, 2018, 42, 2372-2375, incorporated herein by reference in its entirety. ZIF-90 has been utilized recently as a filler for mixed matrix membrane (MMM) applications utilizing MATRIMID, ULTEM, and 6FDA-DAM serving as the polymeric matrices. See T. H. Bae, J. S. Lee, W. Qiu, W. J. Koros, C. W. Jones and S. Nair, *Angewandte Chemie International Edition*, 2010, 49, 9863-9866, incorporated herein by reference in its entirety. The presence of ZIF-90 in these MMMs enhanced gas permeability and selectivity.

However, there is still a need for new materials with selective adsorption of $CO_2$ gas for $CO_2$ capture technologies, in particular, new materials with tunable $CO_2$ adsorption and selectivity properties.

SUMMARY OF THE INVENTION

Accordingly, it is one object of the present invention to provide a hybrid zeolitic imidazolate framework having an isolated purity of at least 95 wt. %, which is a coordination product formed between:
zinc(II) ions;
a linker of formula (I); and
a linker of formula (II);

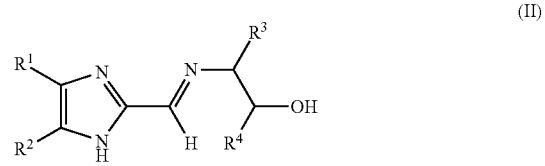

or a stereoisomer or tautomer thereof,
wherein:
each linker of formulae (I) and (II) links together adjacent zinc(II) ions,
$R^1$ and $R^2$ are independently a hydrogen, an optionally substituted alkyl, an optionally substituted aryl, a halo, a nitro, or a cyano, and
$R^3$ and $R^4$ are independently hydrogen, an optionally substituted alkyl, an optionally substituted aryl, or an optionally substituted arylalkyl.

In some embodiments, the hybrid zeolitic imidazolate framework is formed from a relative mol % of the linker of formula (II) of 10 to 75 mol %, based on a total molar amount of the linkers of formulae (I) and (II).

In some embodiments, the hybrid zeolitic imidazolate framework is formed from, each based on a total molar amount of the linkers of formulae (I) and (II):
a relative mol % of the linker of formula (II) of 10 mol %,
a relative mol % of the linker of formula (II) of 25 mol %,
a relative mol % of the linker of formula (II) of 50 mol %, or
a relative mol % of the linker of formula (II) of 75 mol %.
In some embodiments, $R^1$ and $R^2$ are each hydrogen.
In some embodiments, $R^3$ and $R^4$ are each hydrogen.

In some embodiments, the linker of formula (I) is

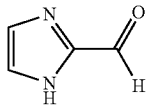

and the linker of formula (II) is

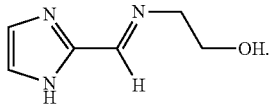

In some embodiments, the hybrid zeolitic imidazolate framework is isoreticular with ZIF-90.

In some embodiments, the hybrid zeolitic imidazolate framework has a BET surface area of 3 to 850 m²/g.

In some embodiments, the hybrid zeolitic imidazolate framework has a micropore volume of 0.05 to 0.25 cm³/g.

In some embodiments, the hybrid zeolitic imidazolate framework has a $CO_2$ uptake capacity of 20 to 95 cm³/g at 273 K and 15 to 47 cm³/g at 298 K, each at 760 Torr.

In some embodiments, hybrid zeolitic imidazolate framework has an ideal selectivity of $CO_2/N_2$ of 25 to 80, and an ideal selectivity of $CO_2/CH_4$ of 5 to 65.

It is another object of the present disclosure to provide a method of making the hybrid zeolitic imidazolate framework involving (i) obtaining a parent zeolitic imidazolate framework formed from coordination between zinc(II) ions and the linker of formula (I); (ii) post-synthetically modifying the parent zeolitic imidazolate framework by reacting a portion of a total number of aldehyde groups present in the parent zeolitic imidazolate framework from the linker of formula (I) with an amino alcohol of formula (III)

$$H_2N-CH(R^3)-CH(R^4)-OH \qquad (III)$$

in an alcoholic solvent to form the hybrid zeolitic imidazolate framework in a reaction mixture; and (iii) isolating the hybrid zeolitic imidazolate framework from the reaction mixture by filtering, washing with an alcohol, and drying at 80 to 120° C.

In some embodiments, the parent zeolitic imidazolate framework is post-synthetically modified with a molar ratio of the amino alcohol of formula (III) to the parent zeolitic imidazolate framework of 0.2:1 to 1.6:1, which provides a relative mol % of the linker of formula (II) of 10 to 75 mol %, based on a total molar amount of the linkers of formulae (I) and (II).

In some embodiments, the amino alcohol of formula (III) is ethanolamine and the linker of formula (I) is

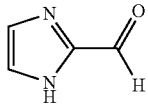

and the linker of formula (II) is

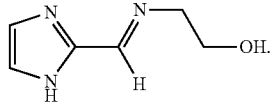

It is yet another object of the present disclosure to provide a method of capturing $CO_2$ from a gas mixture, involving contacting the gas mixture with the hybrid zeolitic imidazolate framework of any embodiment herein to adsorb at least a portion of the $CO_2$ into the hybrid zeolitic imidazolate framework, thereby forming a loaded hybrid zeolitic imidazolate framework and a gas stream depleted in $CO_2$ compared to the gas mixture.

In some embodiments, the gas mixture further comprises at least one other gas selected from the group consisting of hydrogen, oxygen, nitrogen, methane, and carbon monoxide.

In some embodiments, the gas mixture is a pre-combustion gas mixture comprising 15 to 50 vol. % of $CO_2$, based on a total volume of the gas mixture.

In some embodiments, the gas mixture is a post-combustion gas mixture comprising 5 to 15 vol. % of $CO_2$, based on a total volume of the gas mixture.

In some embodiments, the gas mixture has a temperature of −5 to 50° C.

In some embodiments, the gas stream depleted in $CO_2$ contains at least 25% less $CO_2$ by volume compared to a volume of $CO_2$ present in the gas mixture.

BRIEF DESCRIPTION OF THE DRAWINGS

The foregoing paragraphs have been provided by way of general introduction, and are not intended to limit the scope of the following claims. A more complete appreciation of the invention and many of the attendant advantages thereof will be readily obtained as the same becomes better understood by reference to the following detailed description when considered in connection with the accompanying drawings, wherein:

FIG. 5M shows a $^1$H NMR spectrum of the digested ZIF-90 sample showing the presence of 2-carboxyladehyde;

FIGS. 6A-6C illustrate the TGA spectra of parent (pristine) ZIF-90, ZIF-92A (10% PSM-ZIF-90), ZIF-92B (25% PSM-ZIF-90), ZIF-92C (50% PSM-ZIF-90), ZIF-92D (75% PSM-ZIF-90), and ZIF-92 (100% PSM-ZIF-90) at a heating rate of 5° C. min-1 under air flow (FIG. 6A), with an expanded view showing the temperature range of 50 to 300° C. (FIG. 6B) and an expanded view showing the temperature range of 575 to 800° C. (FIG. 6C);

DETAILED DESCRIPTION OF THE INVENTION

Figure 1A:
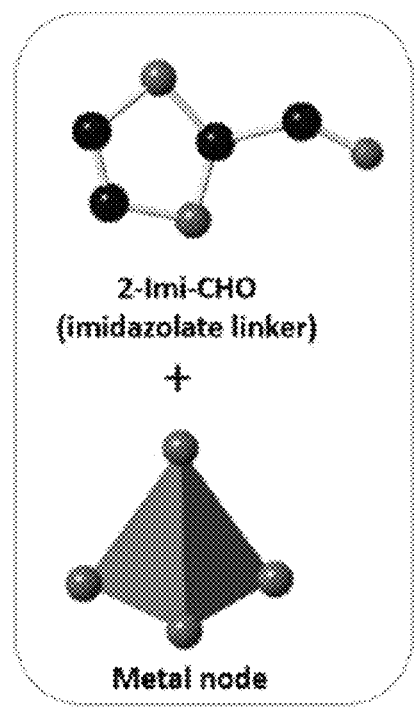
FIG. 1A illustrates representations of the imidazolate linker and the metal node of zeolitic imidazole Framework-90 (ZIF-90)
Figure 1B:
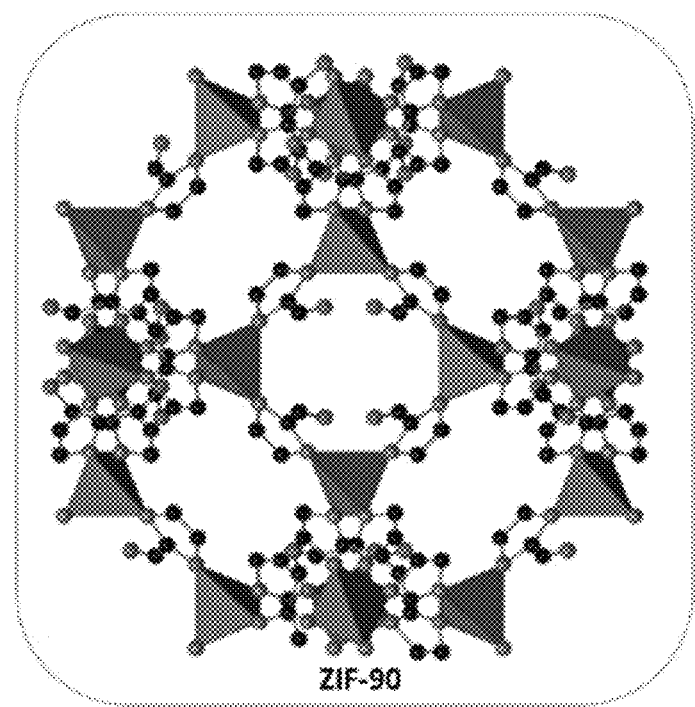
FIG. 1B shows the single crystal structure of ZIF-90, with the characteristic sodalite (sod) topology made of four and six-membered windows leading to a large pore, based on the representations shown in FIG. 1A with H atoms omitted for clarity.
Figure 2:
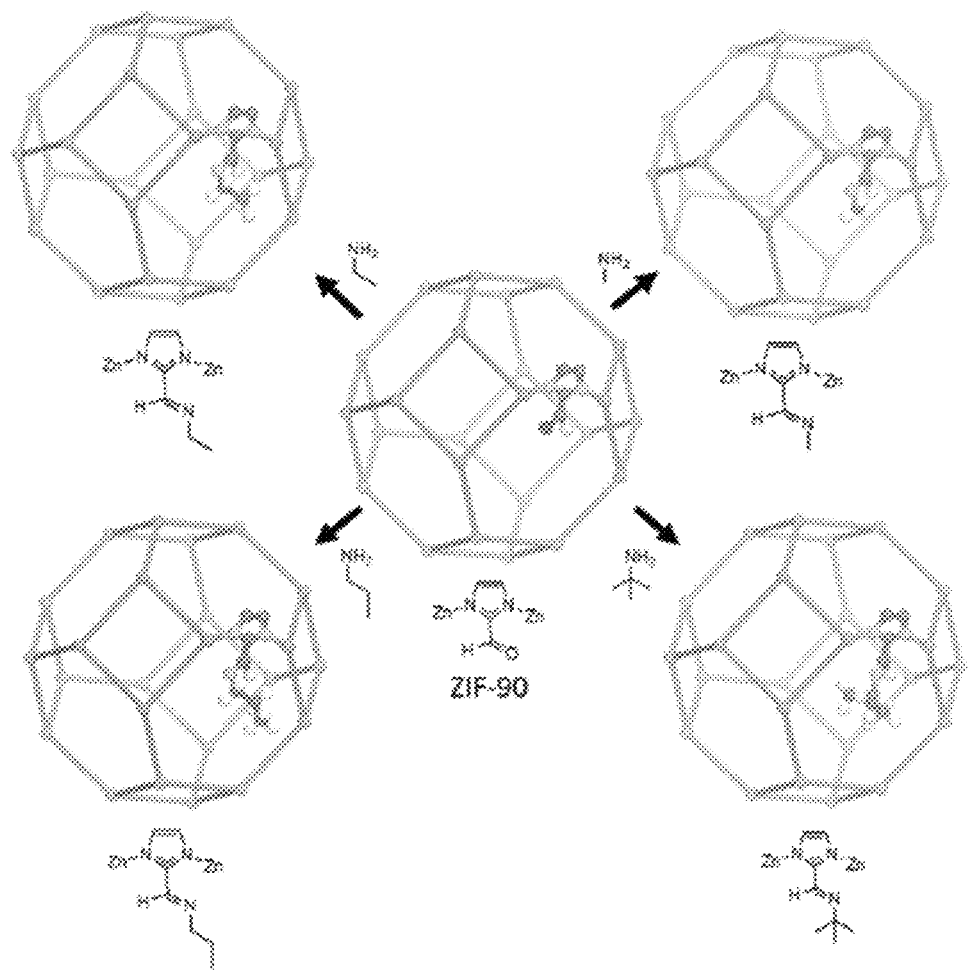
FIG. 2 illustrates post-synthetic modifications (PSM) of ZIF-90 by reacting the ZIF-90 with methylamine, ethylamine, propylamine, and isobutylamine.

In the following description, it is understood that other embodiments may be utilized and structural and operational changes may be made without departure from the scope of the present embodiments disclosed herein.

Definitions

The phrase "substantially free", unless otherwise specified, describes a particular component being present in an amount of less than about 1 wt. %, preferably less than about 0.5 wt. %, more preferably less than about 0.1 wt. %, even more preferably less than about 0.05 wt. %, yet even more preferably 0 wt. %, relative to a total weight of the composition being discussed.

As used herein, the terms "optional" or "optionally" means that the subsequently described event(s) can or cannot occur or the subsequently described component(s) may or may not be present (e.g., 0 wt. %).

The term "alkyl", as used herein, unless otherwise specified, refers to a straight, branched, or cyclic, saturated aliphatic fragment having 1 to 26 carbon atoms, (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, etc.) and specifically includes, but is not limited to, methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, tetradecyl, pentadecyl, hexadecyl, heptadecyl, octadecyl, nonadecyl, eicosyl, guerbet-type alkyl groups (e.g., 2-methylpentyl, 2-ethylhexyl, 2-proylheptyl, 2-butyloctyl, 2-pentylnonyl, 2-hexyldecyl, 2-heptylundecyl, 2-octylodecyl, 2-nonyltridecyl, 2-decyltetradecyl, and 2-undecylpentadecyl), as well as cyclic alkyl groups (cycloalkyls) such as cyclopropyl, cyclobutyl, cyclopentyl, cyclohexyl, norbornyl, and adamantyl.

The term "aryl" means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, anthracenyl, indanyl, 1-naphthyl, 2-naphthyl, and tetrahydronaphthyl. The fused aryls may be connected to another group either at a suitable position on the cycloalkyl/cycloalkenyl ring or the aromatic ring.

The term "arylalkyl", as used herein, refers to a straight or branched chain alkyl moiety (as defined above) that is substituted by an aryl group (as defined above), examples of which include, but are not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

As used herein, the term "substituted" refers to at least one hydrogen atom that is replaced with a non-hydrogen group, provided that normal valencies are maintained and that the substitution results in a stable compound. When a substituent is noted as "optionally substituted", the substituent(s) are selected from alkyl, halo (e.g., chloro, bromo, iodo, fluoro), hydroxyl, alkoxy, oxo, alkanoyl, aryloxy, alkanoyloxy, amino (—$NH_2$), alkylamino (—NHalkyl), cycloalkylamino (—NHcycloalkyl), arylamino (—NHaryl), arylalkylamino (—NHarylalkyl), disubstituted amino (e.g., in which the two amino substituents are selected from alkyl, aryl or arylalkyl, including substituted variants thereof, with specific mention being made to dimethylamino), alkanoylamino, aroylamino, arylalkanoylamino, thiol, alkylthio, arylthio, arylalkylthio, alkylthiono, arylthiono, arylalkylthiono, alkylsulfonyl, arylsulfonyl, arylalkylsulfonyl, sulfonamide (e.g., —$SO_2NH_2$), substituted sulfonamide (e.g., —$SO_2$NHalkyl, —$SO_2$NHaryl, —$SO_2$NHarylalkyl, or cases where there are two substituents on one nitrogen selected from alkyl, aryl, or alkylalkyl), nitro, cyano, carboxy, unsubstituted amide (i.e. —$CONH_2$), substituted amide (e.g., —CONHalkyl, —CONHaryl, —CONHarylalkyl or cases where there are two substituents on one nitrogen selected from alkyl, aryl, or alkylalkyl), alkoxycarbonyl, aryl, guanidine, heterocyclyl (e.g., pyridyl, furyl, morpholinyl, pyrrolidinyl, piperazinyl, indolyl, imidazolyl, thienyl, thiazolyl, pyrrolidyl, pyrimidyl, piperidinyl, homopiperazinyl), and mixtures thereof. The substituents may themselves be optionally substituted, and may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

Throughout the specification and the appended claims, a given chemical formula or name shall encompass all isomers (stereo and optical isomers and racemates) thereof where such isomers exist. Unless otherwise indicated, all chiral (enantiomeric and diastereomeric) and racemic forms are within the scope of the disclosure. Many geometric isomers of C=C double bonds, C=N double bonds, ring systems, and the like can also be present in the compounds, and all such stable isomers are contemplated in the present disclosure. Cis- and trans- (or E- and Z-) geometric isomers of the compounds of the present disclosure are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present disclosure and intermediates made therein are considered to be part of the present disclosure. When enantiomeric or diastereomeric products are prepared, they may be separated by conventional methods, for example, by chromatography, fractional crystallization, or through the use of a chiral agent. Depending on the process conditions the end products of the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric compounds of the present disclosure may be separated into the individual isomers. Compounds of the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure. Further, a given chemical formula or name shall encompass all conformers, rotamers, or conformational isomers thereof where such isomers exist. Different conformations can have different energies, can usually interconvert, and are very rarely isolatable. There are some molecules that can be isolated in several conformations. For example, atropisomers are isomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

As used herein "metal-organic frameworks" or MOFs are compounds having a lattice structure made from (i) metal ions or a cluster of metal ions as vertices ("cornerstones") ("secondary building units" or SBUs) linked together by (ii) organic linkers. The linkers are usually at least bidentate ligands which coordinate to the metal-ions via functional groups such as carboxylates, amines, and/or nitrogen atoms which form part of heterocyclic structures (i.e., nitrogen ring atoms). MOFs are considered coordination polymers made up of (i) the metal ions/clusters and (ii) linker building blocks.

Zeolitic imidazolate frameworks (ZIFs) are a class of metal-organic frameworks that are topologically isomorphic with zeolites. ZIFs are composed of tetrahedrally-coordinated transition metal ions (e.g. Fe, Co, Cu, Zn) connected by imidazolate linkers. Since the metal-imidazole-metal angle is similar to the 145° Si—O—Si angle in zeolites, ZIFs have zeolite-like topologies. Zeolitic imidazolate frameworks which are formed from a combination of two or more different linkers are referred to herein as "hybrid zeolitic imidazolate frameworks" or "hybrid ZIFs".

The term "isoreticular" as used herein is given its ordinary meaning, and thus refers to metal-organic frameworks (MOFs), for example, ZIFs, which have the same network topology.

The term "ideal selectivity" refers to a ratio between the uptake capacity of gases, and can be calculated for example using single component isotherms by Henry's law.

Hybrid zeolitic imidazolate framework (hybrid ZIF)

The present disclosure provides a hybrid zeolitic imidazolate framework (hybrid ZIF) with suitable surface properties (e.g., BET surface area, pore volume, etc.) which enable selective adsorption of $CO_2$ gas for $CO_2$ capture technologies. The hybrid ZIF disclosed herein is easy to manufacture for example using post-synthetic ligand modification strategies, and is stable under a wide range of temperature conditions.

Generally, metal-organic frameworks (MOFs) are composed of two major components, (i) metal ions and (ii) an organic "linker" which coordinates to/connects two (or more) adjacent metal ions to form a coordinated network. The structures may be one- two- or three-dimensional. As such, MOFs may often be referred to as hybrid organic-inorganic materials. The organic linkers are typically multivalent (e.g., di-, tri-, tetra-valent) ligands, and the choice of metal ion and linker dictates the structure and hence properties of the MOF. For example, the metal's coordination preference influences the size and shape of pores by dictating how many ligands can bind to the metal and in which orientation. MOFs usually contain pores (cages) which are present in the voids between the coordinated network of metal ion clusters and organic linker compounds. The pores are typically micropores having a diameter of 2 nm or less, preferably 1.5 nm or less, preferably 1.1 nm or less, preferably 1 nm or less.

Zeolitic imidazolate frameworks (ZIFs) are a class of metal-organic frameworks that are topologically isomorphic with zeolites. ZIFs are composed of tetrahedrally-coordinated transition metal ions (e.g. Fe, Co, Cu, Zn) connected by imidazolate linkers. Since the metal-imidazole-metal angle is similar to the 145° Si—O—Si angle in zeolites, ZIFs have zeolite-like topologies.

The ZIF of the present disclosure is preferably based on zinc ions ($Zn^{2+}$), and at least two different imidazolate linkers (e.g., 2, 3, 4, etc.), preferably two different imidazolate linkers, and is thus referred to herein as a "hybrid" zeolitic imidazolate framework (hybrid ZIF). The hybrid ZIF herein preferably contains predominantly zinc ions with respect to the total metal ion content, with each individual zinc ion being tetrahedrally-coordinated to the imidazolate linkers that constitute the hybrid ZIF. The hybrid zeolitic imidazolate frameworks of the present disclosure preferably contain greater than 50 wt. % of zinc ions, preferably greater than 60 wt. % of zinc ions, preferably greater than 70 wt. % of zinc ions, preferably greater than 80 wt. % of zinc ions, preferably greater than 85 wt. % of zinc ions, preferably greater than 90 wt. % of zinc ions, preferably greater than 95 wt. % of zinc ions, preferably greater than 99 wt. % of zinc ions, preferably 100 wt. % of zinc ions, based on a total weight of metal ions present. If additional metal ions are present (other than zinc ions) these may be present in an amount of less than 50 wt. %, preferably less than 40 wt. %, preferably less than 30 wt. %, preferably less than 20 wt. %, preferably less than 15 wt. %, preferably less than 10 wt. %, preferably less than 5 wt. %, preferably less than 1 wt. %, based on a total weight of metal ions. Additional metal ions may include, but are not limited to, nickel(II) ions, iron(II) ions, copper(II) ions, cobalt(II) ions, and cadmium(II) ions. Such mixed metal ZIFs may be prepared using methods known by those of ordinary skill in the art, for example through post-synthetic metal exchanges.

In preferred embodiments, the hybrid zeolitic imidazolate framework herein is isoreticular with zeolitic imidazolate framework 90 (ZIF-90). ZIF-90 is a zinc-based ZIF that is constructed from tetrahedrally-coordinated zinc(II) ions with a single linker, imidazolate-2-carboxyaldehyde (ICA). ZIF-90 has a crystalline 3D porous framework having a sodalite-type topology. ZIF-90 possesses a large pore size of 1.12 nm that is surrounded by 4- and 6-membered windows (apertures), with the 6-membered window, which has a 0.34 nm diameter, being the only accessible window. ZIF-90 has a BET surface area of 1235 to 1320 m$^2$/g and a micropore volume of 0.62 to 0.69 cm$^3$/g.

The hybrid ZIF of the present disclosure is preferably of the ZIF-90 type, having the same crystal structure and connectivity (topology) as ZIF-90, differing in the partial (incomplete) functionalization of the carboxyaldehyde moiety present on the imidazolate-2-carboxyaldehyde (ICA) linker. Thus, the hybrid ZIF of the present disclosure differs from ZIF-90 by the presence of its partially functionalized framework, which as will become clear, effects its surface properties, reactivity, and ultimately its $CO_2$ uptake/selectivity properties.

The hybrid ZIFs of the present disclosure are the coordination product formed between zinc(II) ions (and optionally additional metal ions) and at least two linkers, preferably two linkers, which each may be bidentate, tridentate, or tetradentate, each linker linking together adjacent zinc ions to form the coordinated network. In preferred embodiments, the linkers are a mixture of formula (I) and formula (II)

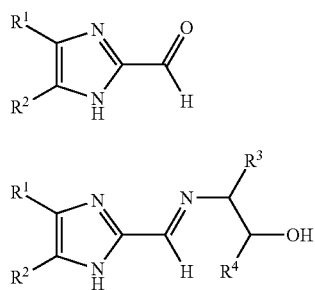

or a stereoisomer or tautomer thereof,
wherein:
$R^1$ and $R^2$ are independently a hydrogen, an optionally substituted alkyl, an optionally substituted aryl, a halo, a nitro, or a cyano, and
$R^3$ and $R^4$ are independently hydrogen, an optionally substituted alkyl, an optionally substituted aryl, or an optionally substituted arylalkyl.

In some embodiments, $R^1$ and $R^2$ are independently hydrogen, an optionally substituted $C_1$ to $C_6$ alkyl, preferably an optionally substituted $C_2$ to $C_5$ alkyl, preferably an optionally substituted $C_3$ to $C_4$ alkyl, preferably an unsubstituted alkyl, for example, methyl, ethyl, or propyl, a halo (e.g., chloro, bromo), or a cyano. $R^1$ and $R^2$ may be the same or different. For example, both $R^1$ and $R^2$ may be hydrogen, an optionally substituted alkyl (e.g., methyl), or chloro. Alternatively, $R^1$ may be cyano while $R^2$ is hydrogen (or vice versa). In preferred embodiments, both $R^1$ and $R^2$ are hydrogen.

In some embodiments, $R^3$ and $R^4$ are independently hydrogen or an optionally substituted alkyl, preferably an optionally substituted $C_1$ to $C_6$ alkyl, preferably an optionally substituted $C_2$ to $C_5$ alkyl, preferably an optionally substituted $C_3$ to $C_4$ alkyl. $R^3$ and $R^4$ may be the same or different. In some embodiments, one of $R^3$ or $R^4$ is an optionally substituted alkyl (e.g., methyl) while the other is hydrogen. For example, $R^3$ may be a methyl and $R^4$ may be hydrogen. In preferred embodiments, $R^3$ and $R^4$ are both hydrogen.

It should be noted that the linker of formula (II) may be present in the hybrid ZIF in its cyclized tautomer form (see formula (IIa) below), and any mention of the linker of formula (II) is intended to also include this cyclized tautomer form (oxazolidine form) when applicable, the relative ratio between such open and cyclized tautomer forms being dependent on the steric environment in the hybrid ZIF, the conditions used to make the hybrid ZIF, as well as environmental factors (e.g., pH, etc.).

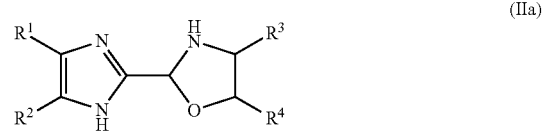

wherein $R^1$-$R^4$ are as described previously.

The hybrid zeolitic imidazolate framework of the present disclosure may be constructed using (i) a single linker or a mixture of two or more linkers that fall within general formula (I) and (ii) a single linker or a mixture of two or more linkers that fall within general formula (II). It is preferred, however, that the hybrid ZIF of the present disclosure is the coordination product resulting from use of (i) a single linker that falls within general formula (I) and (ii) a single linker that falls within general formula (II).

In some embodiments, the hybrid ZIF is a coordination product formed between zinc(II) ions and a mixture of linkers of formulae (I) and (II), whereby a relative mol % of the linker of formula (II) is 10 to 75 mol %, preferably 15 to 70 mol %, preferably 20 to 65 mol %, preferably 25 to 60 mol %, preferably 30 to 55 mol %, preferably 35 to 50 mol %, preferably 40 to 45 mol %, based on a total molar amount of the linkers of formulae (I) and (II). Therefore, in some embodiments, a relative mol % of the linker of formula (I) is 25 to 90 mol %, preferably 30 to 85 mol %, preferably 35 to 80 mol %, preferably 40 to 75 mol %, preferably 45 to 70 mol %, preferably 50 to 65 mol %, preferably 55 to 60 mol %. In preferred embodiments, the ZIF of the present disclosure is formed from 10 mol % of the linker of formula (II) (and 90 mol % of the linker of formula (I)), 25 mol % of the linker of formula (II) (and 75 mol % of the linker of formula (I)), 50 mol % of the linker of formula (II) (and 50 mol % of the linker of formula (I)), or 75 mol % of the linker of formula (II) (and 25 mol % of the linker of formula (I)), each based on a total molar amount of the linkers of formulae (I) and (II). The relative mol % of the linkers of formulae (I) and (II) may be determined through comparative analysis using powdered X-ray diffraction (PXRD), infrared spectra (FTIR), and/or solution or solid-state nuclear magnetic resonance (NMR) techniques as is known to those of ordinary skill in the art. For example, FTIR can be used to determine the relative proportion of functionalization (aldehyde to imine conversion) by measuring the absorption band associated with C=O stretching (e.g., about 1668 cm$^{-1}$) versus the absorption band associated with imine (C=N) bond stretching (e.g., 1637 cm$^{-1}$). For determining the relative mol % of the linkers of formulae (I) and (II) coordinated in a particular ZIF sample using NMR techniques, an NMR spectra (e.g., $^1$H, $^{13}$C, and/or $^{15}$N) may be collected and the relative proportion of the linkers of formulae (I) and (II) may be determined using their respective carboxaldehyde versus imine signals.

In preferred embodiments, the linker of formula (I) is

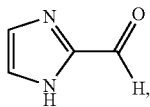

and the linker of formula (II) is

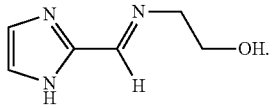

The hybrid zeolitic imidazolate framework of the present disclosure is an isolated product, preferably having an isolated purity of at least 90 wt. %, preferably at least 95 wt. %, preferably at least 96 wt. %, preferably at least 97 wt. %, preferably at least 98 wt. %, preferably at least 99 wt. %, preferably at least 99.5 wt. %. The isolated purity may be determined by methods known to those of ordinary skill in the art, for example, elemental analysis, PXRD, thermogravimetric analysis (TGA), including TGA coupled with evolved gas analysis (EGA), just to name a few, including combinations thereof. While the hybrid ZIF herein may contain relatively small amounts of impurities (<10 wt. %, preferably <5 wt. %), such as entrapped solvent molecules (e.g., methanol, ethanol, isopropanol, water, dimethylformamide, etc.) encountered during manufacture, it is preferably substantially free of reactants such as reactive primary or secondary amines (e.g., ethanolamine), bases (e.g., pyridine, triethylamine, sodium formate, and NaOH), modulating agents, bulk solvents (i.e., large quantities of solvent other than the minor incidental entrapped solvent molecules as described above), and dispersants or particle size/morphology control agents (e.g., poly(ethylene oxide)-poly(propylene oxide)-poly(ethylene oxide), polyvinylpyrrolidone, and poly-(diallyldimethylammonium chloride)) that may be associated with the synthesis thereof.

Owing at least in part to the partial functionalization of the imidazolate-2-carboxyaldehyde (ICA) linker present in ZIF-90 (to form the linker of formula (II)), which without being bound by theory may act to partially obstruct the pores of the ZIF structure, the hybrid ZIF herein may have a reduced BET surface area, and in some cases a drastically reduced BET surface area, compared to parent ZIF-90. For example, the hybrid ZIF herein may have a BET surface area of 3 to 850 m$^2$/g, preferably 5 to 800 m$^2$/g, preferably 10 to 750 m$^2$/g, preferably 15 to 700 m$^2$/g, preferably 20 to 650 m$^2$/g, preferably 25 to 600 m$^2$/g, preferably 30 to 550 m$^2$/g, preferably 35 to 500 m$^2$/g, preferably 40 to 450 m$^2$/g, preferably 45 to 400 m$^2$/g. For example, a hybrid ZIF formed from 10 to 15 mol % of the linker of formula (II) (85 to 90 mol % of the linker of formula (I)) based on a total weight of the linkers may have a BET surface area of 700 to 850 m$^2$/g, preferably 720 to 840 m$^2$/g, preferably 740 to 830 m$^2$/g, preferably 760 to 820 m$^2$/g, preferably 780 to 810 m$^2$/g, preferably 700 to 800 m$^2$/g. Alternatively, a hybrid ZIF formed from 20 to 75 mol % of the linker of formula (II) (25 to 80 mol % of the linker of formula (I)) based on a total weight of the linkers may have a BET surface area of 3 to 75 m$^2$/g, preferably 5 to 70 m$^2$/g, preferably 10 to 65 m$^2$/g, preferably 15 to 60 m$^2$/g, preferably 20 to 55 m$^2$/g, preferably 25 to 50 m$^2$/g.

Further, the hybrid ZIF may have a micropore volume of 0.05 to 0.25 cm$^3$/g, preferably 0.06 to 0.24 cm$^3$/g, preferably 0.08 to 0.22 cm$^3$/g, preferably 0.10 to 0.20 cm$^3$/g, preferably 0.12 to 0.18 cm$^3$/g, preferably 0.14 to 0.16 cm$^3$/g. Both the surface area and pore volume values of the hybrid ZIF of the present disclosure are thus significantly different from those reported for single linker structures such as ZIF-90 (BET surface area of 1235 to 1320 m$^2$/g and a micropore volume of 0.62 to 0.69 cm$^3$/g) and 100% functionalized variants such as ZIF-92, which has no detectable N$_2$ uptake due to severely constricted pore apertures from complete imine functionalization (i.e., ZIF-92 contains no imidazolate-2-carboxyaldehyde (ICA) linker).

In some embodiments, the hybrid zeolitic imidazolate framework of the present disclosure is in the form of particles, for example, particles having a polyhedron morphology and a particle size of 1 to 20 μm, preferably 2 to 19 μm, preferably 3 to 18 μm, preferably 4 to 17 μm, preferably 5 to 16 μm, preferably 6 to 15 μm, preferably 7 to 14 μm, preferably 8 to 13 μm, preferably 9 to 12 μm, preferably 10 to 11 μm. The hybrid ZIF is preferably in the form of monodisperse particles having a particle size described above, with a coefficient of variation or relative standard deviation, expressed as a percentage and defined as the ratio of the particle size standard deviation (σ) to the particle size mean (μ) multiplied by 100 of less than 25%, preferably less than 20%, preferably less than 15%, preferably less than 10%, preferably less than 8%, preferably less than 6%, preferably less than 5%.

The hybrid ZIF described herein also maintains a thermally stability that is comparable to ZIF-90, which allows its use in high temperature gas separation environments. For example, the hybrid ZIF has a % weight loss of no more than 20%, preferably no more than 15%, preferably no more than 10%, preferably no more than 5%, when heated in oxygen up to 350° C.

The hybrid zeolitic imidazolate framework of the present disclosure has an effective adsorption capacity for CO$_2$, which can be determined by thermodynamic, low pressure, single component gas adsorption isotherms. For example, the hybrid ZIF may have a CO$_2$ uptake capacity of 20 to 95 cm$^3$/g, preferably 30 to 91 cm$^3$/g, preferably 35 to 86 cm$^3$/g, preferably 45 to 80 cm$^3$/g, preferably 55 to 75 cm$^3$/g at 273 K and 760 Torr. The hybrid ZIF may have a CO$_2$ uptake capacity of 15 to 47 cm$^3$/g, preferably 20 to 46 cm$^3$/g, preferably 25 to 45 cm$^3$/g, preferably 35 to 44 cm$^3$/g, preferably 40 to 43 cm$^3$/g, preferably 42 to 42.5 cm$^3$/g at 298 K and 760 Torr. For comparison, (at 760 Torr) ZIF-90 has a CO$_2$ uptake capacity of 98.44 cm$^3$/g and 48.57 cm$^3$/g at 273 K and 298 K, respectively, while ZIF-92 has a CO$_2$ uptake capacity of 10.04 cm$^3$/g and 8.63 cm$^3$/g at 273 K and 298 K, respectively.

Despite having a reduced BET surface area and micropore volume compared to ZIF-90, it has been surprisingly found that hybrid ZIFs of the present disclosure that are formed from 10 to 25 mol % of the linker of formula (II) (the remaining percent being the linker of formula (I)), preferably 12 to 23 mol %, preferably 14 to 21 mol %, preferably 16 to 19 mol %, have a higher $CO_2$ uptake capacity than ZIF-90 at all pressures up to 200 Torr. For example, the hybrid ZIFs having the above relative mol percentages of the linker of formula (II) have a $CO_2$ uptake capacity that is 10 to 20% higher, preferably 11 to 19% higher, preferably 12 to 18% higher, preferably 13 to 17% higher, preferably 14 to 16% higher than ZIF-90 at pressures of 60 to 160 Torr.

The hybrid zeolitic imidazolate framework of the present disclosure is selective towards adsorption of $CO_2$ and is therefore useful for various $CO_2$ capture applications. For example, the hybrid zeolitic imidazolate framework may have an ideal selectivity of $CO_2/N_2$ of 25 to 80, preferably 30 to 78, preferably 35 to 70, preferably 40 to 65, preferably 42 to 60, preferably 44 to 50, as well as an ideal selectivity of $CO_2/CH_4$ of 5 to 65, preferably 7 to 60, preferably 7.5 to 50, preferably 10 to 40, preferably 12 to 30, preferably 12.5 to 20, as calculated using single component isotherms by Henry's law. For comparison, ZIF-90 has an ideal selectivity of $CO_2/N_2$ and $CO_2/CH_4$ of 23.6 and 11.3, respectively, while ZIF-92 has no measurable selectivity of $CO_2/N_2$ and $CO_2/CH_4$.

A Method of Making the Hybrid Zeolitic Imidazolate Framework (Hybrid ZIF)

The present disclosure also provides methods for making the hybrid zeolitic imidazolate frameworks. Preferably, post-synthetic modification methods are utilized to construct the hybrid ZIFs described herein. Generally, a parent zeolitic imidazolate framework made from zinc ions and only a linker of formula (I) may be obtained, for example purchased or synthesized through various techniques, including solvothermal synthesis techniques, then the parent zeolitic imidazolate framework may be post-synthetically modified by subjecting a portion of a total number of aldehyde functional groups from the linker of formula (I) with a reactive amine to form the hybrid ZIF containing a mixture of linker types (those of formula (I) and those of formula (II)) in a reaction mixture. The hybrid ZIF may then be isolated in high purity after being removed from the reaction mixture, washed, and dried.

In some embodiments, the parent zeolitic imidazolate framework is synthesized solvothermally. Here, the parent zeolitic imidazolate framework is constructed from a single linker by mixing together a zinc(II) salt and a linker of formula (I), for example, imidazole-2-carboxaldehyde, in a polar aprotic solvent to form a complexation mixture. A concentration of the zinc(II) salt in the complexation mixture may range from 0.01 to 0.15 M, preferably 0.02 to 0.14 M, preferably 0.04 to 0.13 M, preferably 0.06 to 0.12 M, preferably 0.08 to 0.11 M, preferably 0.09 to 0.1 M. The zinc(II) salt may include, but is not limited to, zinc(II) chloride, zinc(II) bromide, zinc(II) iodide, zinc(II) fluoride, zinc(II) nitrate, zinc(II) perchlorate, zinc(II) tetrafluoroborate, zinc(II) oxalate, and zinc(II) fluoride, preferably zinc (II) nitrate, as well as hydrates thereof.

In some embodiments, a concentration of the linker of formula (I) in the complexation mixture is 0.2 to 0.6 M, preferably 0.26 to 0.54 M, preferably 0.28 to 0.52 M, preferably 0.3 to 0.5 M, preferably 0.32 to 0.48 M, preferably 0.34 to 0.46 M, preferably 0.36 to 0.44 M. In some embodiments, a molar ratio of the linker of formula (I) to the zinc (II) salt in the complexation mixture is from 3.8:1 to 4.2:1, preferably 3.9:1 to 4.1:1, preferably 4:1.

The polar aprotic solvent may include, but is not limited to, dimethylformamide (DMF), diethylformamide, N-methyl-2-pyrrolidone, dimethyl sulfoxide, acetone, acetonitrile, dimethylacetamide, and 1,3-dimethyl-2-imidazolidinone, preferably dimethylformamide.

Any desirable modulating agent (e.g., acetic acid, formic acid, benzoic acid, trifluoroacetic acid, and hydrochloric acid, etc.), base (e.g., pyridine, triethylamine, sodium formate, and NaOH, etc.), and/or dispersant or particle size/morphology control agent (e.g., poly(ethylene oxide)-poly (propylene oxide)-poly(ethylene oxide), polyvinylpyrrolidone, and poly-(diallyldimethylammonium chloride), etc.) may be optionally added to the complexation mixture, although such components are preferably not employed in the methods herein.

Next, the complexation mixture may be heated with agitation (e.g., stirring, shaking, sonication, etc.), for example heated under solvothermal conditions in an acceptable vial, vessel, or autoclave to a temperature of 60 to 150° C., preferably 65 to 140° C., preferably 70 to 130° C., preferably 75 to 120° C., preferably 80 to 110° C., for 1 to 24 hours, preferably 2 to 12 hours, preferably 4 to 8 hours, preferably 6 to 7 hours, or until the complexation mixture becomes clear and reaction is deemed complete. Under such coordination conditions, the parent zeolitic imidazolate framework may be formed by self-assembly of the zinc ions and the linker of formula (I). It is preferred that the parent zeolitic imidazolate framework herein is formed by self-assembly, and thus the methods of the present disclosure do not require the use of surfactants, structure-directing agents, particle size/morphology control agents, complexing agents, or templating agents.

After the complexation is deemed sufficiently complete, an alcoholic solvent such as methanol, ethanol, isopropanol, etc. may then be added to the complexation mixture, thereby slowly turning the complexation mixture turbid. The resulting mixture may be agitated (stirred, shaken, sonicated, etc.), at 40 to 100° C., preferably 45 to 90° C., preferably 50 to 80° C. for 12 to 72 hours, preferably 20 to 48 hours, preferably 24 to 32 hours. Thereafter, the parent zeolitic imidazolate framework may be collected using any known solid-liquid separation technique (e.g., filtration, decantation, centrifugation, etc.), preferably centrifugation, preferably by centrifugation at 4,000 to 8,000 rpm, preferably 5,000 to 7,000 rpm, preferably 6,000 rpm, and optionally washed with an alcoholic solvent (e.g., methanol). The parent zeolitic imidazolate framework may be dried under vacuum and at elevated temperature, for example, at 70 to 130° C., preferably 80 to 120° C., preferably 90 to 110° C., preferably 100° C., in order to substantially remove solvent molecules that may remain in the pores, although such a drying/desorption step is optional.

After obtaining the parent zeolitic imidazolate framework, the parent zeolitic imidazolate framework is then subject to post-synthetic modification by reacting a portion of a total number of aldehyde groups (but not all aldehyde groups) present in the parent zeolitic imidazolate framework (from the linker of formula (I)) with an amino alcohol of formula (III)

$$H_2N-CH(R^3)-CH(R^4)-OH \qquad (III)$$

wherein $R^3$ and $R^4$ are as described previously, to form the hybrid zeolitic imidazolate framework of the present disclosure having a mixture of coordinated linkers of formulae (I)

and (II). In preferred embodiments, the amino alcohol of formula (III) is ethanolamine ($H_2NCH_2CH_2OH$).

The post-synthetic modification step may be performed by suspending the parent zeolitic imidazolate framework in an alcoholic solvent, including, but not limited to, methanol, ethanol, and isopropanol, in the presence of the amino alcohol of formula (III) to form a reaction mixture. A concentration of the parent zeolitic imidazolate framework in the alcoholic solvent may range from 0.005 to 0.1 M, preferably 0.01 to 0.09 M, preferably 0.015 to 0.08 M, preferably 0.02 to 0.07 M, preferably 0.025 to 0.06 M, preferably 0.03 to 0.05 M. In preferred embodiments, a molar ratio of the amino alcohol of formula (III) to the parent zeolitic imidazolate framework used for partial linker modification ranges from 0.2:1 to 1.6:1, preferably 0.25:1 to 1.5:1, preferably 0.3:1 to 1.4:1, preferably 0.35:1 to 1.3:1, preferably 0.4:1 to 1.2:1, preferably 0.45:1 to 1.1:1, preferably 0.5:1 to 1:1, preferably 0.55:1 to 0.9:1, preferably 0.6:1 to 0.8:1, preferably 0.65:1 to 0.7:1, which provides a relative mol % of the linker of formula (II) as described previously (e.g., 10 to 75 mol %).

The reaction mixture may then be heated to 40 to 100° C., preferably 50 to 90° C., preferably 55 to 80° C., preferably 60 to 75° C., preferably 65 to 70° C., or to the reflux temperature of the alcoholic solvent for 2 to 72 hours, preferably 10 to 48 hours, preferably 18 to 24 hours form the hybrid ZIF.

The reaction mixture may then be optionally cooled to room temperature, and the hybrid zeolitic imidazolate framework may be isolated by any known solid-liquid separation technique (e.g., filtration, decantation, centrifugation, etc.), preferably filtration. The isolated hybrid ZIF may then be washed with an alcohol such as methanol, ethanol, and isopropanol, which may be the same or different from the alcoholic solvent, preferably the same. The washing may be performed by washing the isolated hybrid ZIF with the alcohol at least once, preferably at least twice, preferably at least three times, followed by soaking the isolated hybrid ZIF in the alcohol for an extended period, for example, for 8 to 72 hours, preferably 12 to 48 hours, preferably 18 to 24 hours in order to purify and/or exchange any high boiling components entrapped within the framework such as high boiling solvents (e.g., dimethylformamide, water, etc.), unreacted reactants (e.g., ethanolamine), or any other material encountered during manufacture, with the alcohol. Preferably methanol is employed as the alcohol. Finally, drying may be performed at 80 to 120° C., preferably 90 to 110° C., preferably 100° C. for 8 to 72 hours, preferably 12 to 48 hours, preferably 18 to 24 to substantially remove the residual alcohol (e.g., methanol) to provide the hybrid ZIF of the present disclosure having an isolated purity described previously (>95%).

A Method of Capturing $CO_2$

The present disclosure also provides a method of capturing $CO_2$ from a gas mixture with the hybrid ZIF disclosed herein. The methods herein can be used for the capture of $CO_2$ from large point sources, such as large fossil fuel or biomass electricity power plants, industries with major $CO_2$ emissions, natural gas processing, synthetic fuel plants, and fossil fuel-based hydrogen production plants. Capture from the open atmosphere is also possible. Therefore, the hybrid ZIF may be useful in $CO_2$ removal/capture from various gas mixtures that contain carbon dioxide ($CO_2$) and at least one other gas. The other gas may include, but is not limited to, nitrogen, hydrogen, oxygen, water (vapor), carbon monoxide, hydrocarbons having 1-4 carbon atoms (e.g. methane, ethane, ethylene, acetylene, propane, propylene, butane, iso-butane), nitrogen oxides (i.e. nitric oxide, nitrous oxide, nitrogen dioxide), and noble gases (e.g. helium, neon, argon, krypton, xenon), including mixtures thereof. In preferred embodiments, the other gas is one or more of hydrogen, oxygen, nitrogen, methane, and carbon monoxide, more preferably one or more of nitrogen and methane.

The hybrid ZIF of the present disclosure may be well-suited for applications where fossil fuels are burned for electricity. For example, the gas mixture may be a pre-combustion gas mixture, that is, a gas mixture produced from de-carbonizing a fuel source prior to combustion taking place. Pre-combustion processing is typically used in the production of fertilizer, chemical gaseous fuel ($H_2$, $CH_4$), cement processing, and power production facilities (e.g., biomass power plant), and the like. For example, in gasification processes a feedstock (such as coal) is partially oxidized in steam and oxygen/air under high temperature and pressure, for instance in a gasifier, to form synthesis gas. This synthesis gas, or syngas, is a mixture of hydrogen, carbon dioxide ($CO_2$) and smaller amounts of other gaseous components, such as methane. Syngas is an important intermediate for production of hydrogen, ammonia, methanol, and synthetic hydrocarbon fuels, and can be produced from many sources, including natural gas, coal, biomass, or virtually any hydrocarbon feedstock, by reaction with steam (steam reforming), carbon dioxide (dry reforming), or oxygen (partial oxidation). For example, syngas can be subject to the water-gas shift reaction to convert CO and water to $H_2$ and $CO_2$, producing a $H_2$ and $CO_2$-rich gas mixture. The $CO_2$ can then be captured and separated, transported, and ultimately sequestered or processed, and the $H_2$-rich fuel combusted. Syngas is also used as an intermediate in producing synthetic petroleum for use as a fuel or lubricant via the Fischer-Tropsch process and previously the Mobil methanol to gasoline process. In some embodiments, the method is applied to remove/capture $CO_2$ from a pre-combustion gas mixture, for example a pre-combustion gas mixture having a $CO_2$ concentration of 15 to 50 vol. %, preferably 20 to 45 vol. %, preferably 25 to 40 vol. %, preferably 30 to 35 vol. %, based on a total volume of the (pre-combustion) gas mixture.

Alternatively, the gas mixture may be a post-combustion gas mixture, i.e., a gas mixture produced after combustion of a fossil fuel, for example the gas mixture may be an exhaust (flue) gas from a power station or other large point source. In some embodiments, the method is applied to remove/capture $CO_2$ from a post-combustion gas mixture, for example a post-combustion gas mixture having a $CO_2$ concentration of 5 to 15 vol. %, preferably 6 to 14 vol. %, preferably 7 to 13 vol. %, preferably 8 to 12 vol. %, preferably 9 to 11 vol. %, preferably 10 vol. %, based on a total volume of the (post-combustion) gas mixture. Additionally, the post-combustion gas mixture may also include 70 to 75 vol. %, preferably 71 to 74 vol. %, preferably 72 to 73 vol. % of $N_2$ and 5 to 7 vol. %, preferably 5.5 to 6.5 vol. %, preferably 6 vol. % $H_2O$, each based a total volume of the (post-combustion) gas mixture. In preferred embodiments, the $CO_2$-capturing methods herein are performed post-combustion, i.e., the gas mixture is a post-combustion gas mixture, for example, a flue gas.

The $CO_2$ capture/removal methods of the present disclosure may be performed by contacting the gas mixture with the hybrid zeolitic imidazolate framework disclosed herein to adsorb at least a portion of the $CO_2$ into/onto the hybrid zeolitic imidazolate framework, thereby forming a loaded hybrid zeolitic imidazolate framework and a gas stream depleted in $CO_2$ compared to the gas mixture.

Adsorption technologies may be employed herein for $CO_2$ capture, for example, the $CO_2$ may be adsorbed by the hybrid ZIF via a physisorption process, meaning the process is primarily physical and preferably no chemical changes occur on the hybrid ZIF or to the $CO_2$ molecules. As such, the hybrid ZIF may be freestanding or supported on or within a substrate, for example, the hybrid ZIF may be housed within a chamber, for example, a column, plug, or filter, and/or on a substrate such as silica, alumina, and the like. Preferably, the hybrid ZIF may be supported within a fixed-bed column.

The chamber may be of any shape so long as the hybrid ZIF can be securely housed and utilized inside the chamber to accomplish the gas adsorption. The chamber may include an inlet configured to accept a feed stream (gas mixture), a gas stream outlet configured to expel a permeate (a gas stream depleted in $CO_2$), and optionally a retentate outlet configured to expel a retentate (a $CO_2$ rich stream). The chamber can be configured to be pressurized so as to force the gas mixture though the inlet and through a bed of the hybrid ZIF (and optionally a support) to enable infusion of $CO_2$ present in the gas mixture into the pore spaces of the hybrid ZIF, thereby forming the loaded hybrid zeolitic imidazolate framework. The chamber may also be connected to a vacuum pump to provide vacuum or a reduced pressure to the gas stream outlet for a similar purpose.

Membrane gas separation technologies may also be employed herein for $CO_2$ capture, for example, the hybrid ZIF may be utilized in a mixed matrix membrane by homogeneously interpenetrating the hybrid ZIF of the present disclosure within a polymer matrix, along with other optional filler materials. In such cases, the hybrid zeolitic imidazolate framework may be present in an amount of 0.1 to 50 wt. %, preferably 0.5 to 40 wt. %, preferably 1 to 30 wt. %, preferably 2 to 20 wt. %, preferably 3 to 15 wt. %, preferably 4 to 10 wt. %, preferably about 5 wt. %, relative to a total weight of the membrane.

The membrane may be a thin film membrane (e.g., a thickness of 10 to 2,000 μm), a flat sheet membrane, a spiral membrane, a tubular membrane, or a hollow fiber membrane. The membrane may be in the form of various shapes, for example, flat (e.g., for a disc-shaped membrane), bent, curved (e.g., a cylinder shaped membrane), and rippled. The membrane may have a porous morphology. For example, the membrane may contain unconnected pores each representing an isolated cavity having an unbroken pore wall, with the pores extending through the membrane without intersecting one another (e.g., monolithic membrane). Alternatively, the membrane may contain pores which are part of an interconnected network of pores where the pores in the membrane are randomly oriented and intersect. The membrane may contain micropores (an average diameter of less than 2 nm), mesopores (an average diameter of 2-50 nm), macropores (an average diameter larger than 50 nm), or a mixture thereof. For example, the membrane may be macroporous, having pores with an average diameter in a range of 0.5 to 10 μm, preferably 1 to 8 μm, preferably 1.5 to 6 μm, preferably 2 to 5 μm, preferably 3 to 4 μm.

The polymer matrix preferably has a high glass transition temperature ($T_g$), high melting point, and high crystallinity, i.e., the polymer is preferably a rigid, glassy polymer. In some embodiments, the polymer (of the polymer matrix) has a weight average molecular weight ($M_w$) of $1\times10^4$ to $2\times10^7$ g/mol, preferably $5\times10^4$ to $1.5\times10^7$ g/mol, preferably $1\times10^5$ to $1\times10^7$ g/mol.

Exemplary polymers that may be used to construct the polymer matrix in the disclosed mixed matrix membranes include, but are not limited to:
- polyolefins such as polyethylene, polypropylene, polybutene-1, and poly(4-methyl pentene-1), including polyvinyls and fluoropolymer variants thereof, for example polyvinylidene fluoride (PVDF), polytetrafluoroethylene (PTFE), polyvinyl chloride, polyvinyl fluoride, polyvinylidene chloride, polyvinylidene fluoride, polyvinyl alcohol, polyvinyl ester (e.g., polyvinyl acetate and polyvinyl propionate), polyvinyl pyridine, polyvinyl pyrrolidone, polyvinyl ether, polyvinyl ketone, polyvinyl aldehyde (e.g., polyvinyl formal and polyvinyl butyral), polyvinyl amide, polyvinyl amine, polyvinyl urethane, polyvinyl urea, polyvinyl phosphate, and polyvinyl sulfate;
- polystyrene (e.g., isotactic polystyrene and syndiotactic polystyrene), including styrene-containing copolymers such as acrylonitrilestyrene copolymers, styrene-butadiene copolymers and styrene-vinylbenzylhalide copolymers;
- thermoplastic elastomers (TPE);
- silicones such as polydimethylsiloxane (PDMS) and polymethylphenylsilicone (PMPS);
- polyacetylenes such as polytrimethylsilylpropyne;
- polysulfones including polyethersulfones (PESs) as well as sulfonated PESs, with specific mention being made to poly(1,4-phenylene ether-ether-sulfone), poly(1-hexadecene-sulfone), poly(l-tetradecene-sulfone), poly(oxy-1,4phenylenesulfonyl-1,4-phenylene), poly(oxy-1,4-phenylenesulfonyl-1,4-phenylene), poly(oxy-1,4-phenylenesulfonyl-1,4-phenylene), poly(oxy-1,4-phenylenesulfonyl-1,4-phenylene), polyphenylsulfone, and ULTRASON S 6010 from BASF;
- polysulfonamides such as poly[1-[4-(3-carboxy-hydroxyphenylazo)benzenesulfonamido]-1,2-ethanediyl]);
- polyacetals;
- polyethers;
- polyethylenimines;
- polycarbonates;
- cellulosic polymers such as cellulose acetate, cellulose triacetate, cellulose acetate-butyrate, cellulose propionate, ethyl cellulose, methyl cellulose, and nitrocellulose;
- polyamides including aromatic polyamides and aliphatic polyamides, such as Nylon 6 and polyphthalamide;
- polyimides with specific mention being made to KAPTON (poly (4,4'-oxydiphenylene-pyromellitimide) by DuPont, MATRIMID by Huntsman Advanced Materials, P84 by HP Polymers GmbH, poly(3,3',4,4'-benzophenone tetracarboxylic dianhydride-pyromellitic dianhydride-3,3',5,5'-tetramethyl-4,4'-methylene dianiline) (or poly(BTDA-PMDA-TMMDA)), poly(3,3',4,4'-benzophenone tetracarboxylic dianhydride-pyromellitic dianhydride-4,4'-oxydiphthalic anhydride-3,3',5,5'-tetramethyl-4,4'-methylene dianiline) (or poly(BTDA-PMDA-ODPA-TMMDA)), poly(3,3',4,4'-diphenylsulfone tetracarboxylic dianhydride-3,3',5,5'-tetramethyl-4,4'-methylene dianiline) (or poly(DSDA-TMMDA)), poly(3,3',4,4'-benzophenone tetracarboxylic dianhydride-3,3',5,5'-tetramethyl-4,4'-methylene dianiline) (or poly(BTDA-TMMDA)), poly(3,3',4,4'-diphenylsulfone tetracarboxylic dianhydride-pyromellitic dianhydride-3,3',5,5'-tetramethyl-4,4'-methylene dianiline) (or poly(DSDA-PMDA-TMMDA)), and poly[2,2'-bis-(3,4-dicarboxyphenyl) hexafluoropropane dianhydride-2,2-bis(3-amino-4-hydroxyphenyl)-hexafluoropropane] (or poly(6FDA-APAF)), poly[2,2'-bis-(3,4-dicarboxyphenyl) hexafluoropropane dianhydride-2,4,6-trimethyl-1,3-phenylenediamine] (or poly(6FDA-DAM), poly[3,3',4,4'-benzophenonetetracarboxylic dianhydride-2,2-bis (3-amino-4-hydroxyphenyl)-hexafluoropropane] (or poly(BTDA-APAF)), poly(3,3',4,4'-benzophenonetetracarboxylic dianhydride-3,3'-dihydroxy-4,4'-diaminobiphenyl) (or poly(BTDA-HAB)), poly[4,4'-oxydiphthalic anhydride-2,2-bis(3-amino-4-hydroxyphenyl)-hexafluoropropane] (or poly(ODPA-APAF)), poly[3,3',4,4'-diphenylsulfone tetracarboxylic dianhydride-2,2-bis(3-amino-4-hydroxyphenyl)-hexafluoropropane] (or poly(DSDA-APAF)), poly(3,3',4,4'-diphenylsulfone tetracarboxylic dianhydride-3,3'-dihydroxy-4,4'-diamino-biphenyl) (or poly(DSDA-HAB)), poly[2,2'-bis-(3,4-dicarboxyphenyl) hexafluoropropane dianhydride-3,3',4,4'-benzophenonetetracarboxylic dianhydride-2,2-bis(3-amino-4-hydroxyphenyl)-hexafluoropropane] (or poly(6FDA-BTDA-APAF)), poly[4,4'-oxydiphthalic anhydride-2,2-bis(3-amino-4-hydroxyphenyl)-hexafluoropropane-3,3'-dihydroxy-4,4'-diamino-biphenyl] (or poly(ODPA-APAF-HAB)), poly[3,3',4,4'-benzophenonetetracarboxylic dianhydride-2,2-bis(3-amino-4-hydroxyphenyl)-hexafluoropropane-3,3'-dihydroxy-4,4'-diamino-biphenyl] (or poly(BTDA-APAF-HAB)), poly[2,2'-bis-(3,4-dicarboxyphenyl) hexafluoropropane dianhydride-3,3'-dihydroxy-4,4'-diamino-biphenyl] (or poly(6FDA-HAB)), and poly(4,4'-bisphenol A dianhydride-3,3',4,4'-benzophenonetetracarboxylic dianhydride-2,2-bis(3-amino-4-hydroxyphenyl)-hexafluoropropane) (or poly(BPADA-BTDA-APAF));

polyetherimides such as ULTEM products manufactured by Sabic Innovative Plastics;
polyamide imides;
polyketones;
polyether ketones such as polyether ether ketone, sulfonated polyether ether ketone and the like;
polyarylene oxides such as polyphenylene oxide, polyxylene oxide, sulfonated polyxylene oxide and brominated polyxylene oxide;
polyurethanes;
polyureas;
polyazomethines;
polyesters including polyarylates such as polyethylene terephthalate and polyphenylene terephthalate;
acrylates such as polyalkyl (meth)acrylate, polyacrylate, polyacrylate-polyacrylamide copolymers;
polysulfides;
heterocyclic thermoplastics such as polybenzimidazoles, polyoxadiazoles, polytriazoles, polybenzoxazole, and polybenzimidazole;
polycarbodiimides;
polyphosphazines;
polyhydrazides;
and copolymers thereof, including block copolymers, grafts, and blends thereof.

The mixed matrix membrane may be made by methods known to those of ordinary skill in the art, for example, by casting or melt blending, and the polymer matrix may be made porous by known techniques including, but not limited to, irradiation, stretching of a melt-processed semi-crystalline polymer substrate, vapor-induced phase separation, and temperature-induced phase separation, just to name a few.

When the hybrid zeolitic imidazolate framework of the present disclosure is utilized in mixed matrix membrane separation technologies, the membrane may be housed in chamber such that the membrane divides the chamber into a feed side and a permeate side. The gas mixture may then be fed into the feed side of the chamber so that at least a portion of the $CO_2$ present in the gas mixture permeates the membrane and is adsorbed by the hybrid ZIF, thereby forming the loaded hybrid ZIF. This may be accomplished for example by supplying the gas mixture at above atmospheric pressure or otherwise forcing at least a portion of the gas mixture through the membrane by pressurizing the feed side, or applying a vacuum to the permeate side of the chamber. A gas stream depleted in $CO_2$ compared to the gas mixture may then be collected from the permeate side, and the chamber may be optionally configured to include a retentate outlet to expel a retentate (a $CO_2$ rich stream) after desorbing $CO_2$ molecules from the loaded hybrid ZIF.

Regardless of whether an adsorptive technique (e.g., fixed-bed of the hybrid ZIF) or a membrane gas separation technology is utilized, the gas mixture is contacted with the hybrid ZIF disclosed herein. The gas mixture may be contacted with the hybrid ZIF in a single chamber, or the gas mixture may be passed through a series of chambers housing the hybrid ZIF to gradually/sequentially remove/capture $CO_2$ from the gas mixture. Similarly, the hybrid ZIF may be used in addition to other known adsorption materials to provide a gas stream depleted in $CO_2$ and a loaded hybrid zeolitic imidazolate framework.

In some embodiments, prior to contacting the gas mixture with the hybrid ZIF, the hybrid ZIF is activated through a degassing procedure performed in a sub-atmospheric pressure of 0.05 to 0.8 atm, preferably 0.1 to 0.5 atm, preferably 0.2 to 0.4 atm to remove gas or solvent molecules that may reside in the pore spaces of the hybrid ZIF. The hybrid ZIF may be degassed at a temperature of 0 to 200° C., preferably 10 to 150° C., preferably 25 to 100° C., or about 80° C. for 1 to 48 hours, preferably 2 to 36 hours, preferably 8 to 24 hours, preferably 12 to 18 hours.

A force may be provided to deliver the gas mixture into contact with the hybrid ZIF. The gas mixture may be introduced at flow rate of 0.001 to 1,000 L/min, preferably 0.005 to 500 L/min, preferably 0.01 to 100 L/min, preferably 0.05 to 10 L/min, preferably 0.1 to 5 L/min, preferably 0.5 to 2 L/min. In some embodiments, the gas mixture is pressurized (e.g., be applying pressure to a feed side of a chamber) at a pressure of greater than 760 and up to 4,000 Torr, preferably 800 to 3,500 Torr, preferably 850 to 3,000 Torr, preferably 900 to 2,500 Torr, preferably 1,000 to 2,000 Torr to force at least a portion of the gas mixture to contact the hybrid ZIF. In some embodiments, the gas mixture is contacted with the hybrid ZIF under vacuum, for example by applying a reduced pressure of less than 760 Torr, preferably 10 to 750 Torr, preferably 20 to 700 Torr, preferably 30 to 600 Torr to the permeate side of a chamber such that at least a portion of the gas mixture is brought into contact with the hybrid ZIF. In preferred embodiments, the gas mixture is contacted with the hybrid ZIF under vacuum at a reduced pressure of 60 to 160 Torr, preferably 70 to 150 Torr, preferably 80 to 140 Torr, preferably 90 to 130 Torr, preferably 100 to 120 Torr. Alternatively, the gas mixture may stay stagnant over the hybrid ZIF (i.e. as an atmosphere to the hybrid ZIF) for a suitable amount of time to enable adsorption of $CO_2$.

The gas mixture may be contacted with the hybrid zeolitic imidazolate framework at any temperature that enables desired levels of $CO_2$ capture, for example, the gas mixture may have a temperature of −5 to 50° C., preferably 0 to 45°

C., preferably 5 to 40° C., preferably 10 to 35° C., preferably 20 to 30° C., preferably 25 to 28° C.

A gas stream depleted in $CO_2$ may be obtained after at least a portion of $CO_2$ is adsorbed onto the hybrid ZIF. A composition of the gas stream depleted in $CO_2$ may vary depending on the composition of the gas mixture. In some embodiments, the gas stream depleted in $CO_2$ contains at least 25% less $CO_2$, preferably at least 30% less $CO_2$, preferably at least 40% less $CO_2$, preferably at least 50% less $CO_2$, preferably at least 60% less $CO_2$, preferably at least 70% less $CO_2$, preferably at least 80% less $CO_2$, preferably at least 90% less $CO_2$, preferably at least 95% less $CO_2$, by volume compared to a volume of $CO_2$ present in the gas mixture. For example, when the methods herein are employed in pre-combustion processes, the gas stream depleted in $CO_2$ may contain less than 35 vol % $CO_2$, preferably less than 25 vol % $CO_2$, preferably less than 20 vol % $CO_2$, preferably less than 15 vol % $CO_2$, preferably less than 10 vol % $CO_2$, preferably less than 5 vol % $CO_2$, preferably less than 1 vol % $CO_2$, preferably less than 0.5 vol % $CO_2$, preferably less than 0.1 vol % $CO_2$, based on a total volume of gas stream depleted in $CO_2$. When the methods herein are employed in post-combustion processes, the gas stream depleted in $CO_2$ may contain less than 10 vol % $CO_2$, preferably less than 8 vol % $CO_2$, preferably less than 6 vol % $CO_2$, preferably less than 4 vol % $CO_2$, preferably less than 2 vol % $CO_2$, preferably less than 1 vol % $CO_2$, preferably less than 0.5 vol % $CO_2$, preferably less than 0.1 vol % $CO_2$, preferably less than 0.05 vol % $CO_2$, preferably less than 0.01 vol % $CO_2$, based on a total volume of gas stream depleted in $CO_2$.

In some embodiments, the method of the present disclosure further involves desorbing the $CO_2$ from the loaded hybrid ZIF, and reusing the hybrid ZIF. The carbon dioxide may be stripped off the hybrid ZIF using temperature swing adsorption (TSA) or pressure swing adsorption (PSA) techniques so the hybrid ZIF can be reused. For instance, desorbing the $CO_2$ may involve heating the loaded hybrid ZIF at a temperature of 50 to 200° C., preferably 60 to 180° C., preferably 70 to 160° C., preferably 80 to 140° C., preferably 90 to 120° C., preferably 100 to 110° C., subjecting the loaded hybrid ZIF to a reduced pressure of less than 750 Torr, preferably less than 700 Torr, preferably less than 600 Torr, preferably less than 500 Torr, preferably less than 400 Torr, preferably less than 300 Torr, preferably less than 200 Torr, preferably less than 100 Torr, preferably less than 75 Torr, preferably less than 50 Torr, preferably less than 25 Torr, or a combination of heat and reduced pressure.

The loaded hybrid ZIF may be regenerated (i.e. desorbed) and reused without a significant loss in $CO_2$ uptake capacity. For instance, the hybrid ZIF may be used to capture $CO_2$, desorbed, and reused for up to 25 cycles, preferably up to 20 cycles, preferably up to 15 cycles, preferably up to 10 cycles, preferably up to 5 cycles.

Desorbing the $CO_2$ from the loaded hybrid ZIF generates a gas stream enriched in $CO_2$. Such a gas stream may be optionally subjected to further processing steps such as an additional purification step (e.g. column chromatography, further membrane separation steps, etc.), and any captured and collected $CO_2$ may optionally be subject to numerous processing steps, for example, used for the production of urea, methanol, metal carbonates and bicarbonates, aromatic and aliphatic polycarbonates, and sodium salicylate, as well as used in biotransformations to form fuels such as isobutyraldehyde and isobutanol, as is known to those of ordinary skill in the art.

In addition to pre-combustion and/or post-combustion $CO_2$ capture applications, it is contemplated that the hybrid ZIFs disclosed herein may be used in air purifiers, chemical filters, oil and gas refineries, fermenters, bioreactors, or in any other process where the capture/removal of $CO_2$ is desired.

The examples below are intended to further illustrate protocols for preparing the hybrid ZIFs and for using the hybrid ZIFs in $CO_2$ capture applications, and are not intended to limit the scope of the claims.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

EXAMPLES

Experimental
Materials

All reagents were used as received without further purification. Zinc nitrate ($Zn(NO_3)_2 \cdot 6H_2O$) was purchased from Loba, India, 2-imidazolecarboxaldehyde was purchased from Alfa Aesar, polyimide, polyetherimide and polysulfone, methanol, acetonitrile, N,N'-dimethylformaldehyde, (DMF) was purchased from Sharlu, N,N'-Dimethylacetamide (DMA), hexane, deuterated dimethyl sulfoxide, (DMSO-$d_6$), and deuterium chloride (DCl in $D_2O$). $H_2$ (99.999%), $CH_4$ (99.9%), $C_2H_6$ (99.9%), and $C_3H_8$ (99.9%) were purchased form Abdullah Hashem Industrial Gas Co., Saudi Arabia. $CO_2$ (99.9%), $N_2$ (99.999%), and $O_2$ (99.9%) were purchased from Air Liquide, Dammam, Saudi Arabia. Powder X-ray diffraction (PXRD) patterns were collected on a Rigaku, model employing Ni-filtered Cu K$\alpha$ radiation ($\lambda$=1.54178 Å). Field emission scanning electron microscopy (FESEM) analysis was performed using gold sputtered samples on a TESCAN MIRA3 (10-30 kV accelerating voltage) with energy-dispersive X-ray spectroscopy (EDX). Thermogravimetric analysis (TGA) was conducted using a TA Q500 with the sample held in a platinum pan under airflow. BET surface areas were calculated using Quantachrome Quadrasorb Evo™ gas sorption surface area analyser, volumetric uptake of $CO_2$, $CH_4$ and $N_2$ were tested at Quantachrome Autosorb iQ. $^1H$ and $^{13}C$ nuclear magnetic resonance (NMR) spectroscopy measurements were carried out using a JEOL JNM-LA500 spectrometer at 500 and 125.6 MHz, respectively.

Synthesis of Pristine ZIF-90. ZIF-90 was synthesized by heating at 80° C. a mixture solution of imidazole-2-carboxyaldehyde (2.688 g) and $Zn(NO_3)_2 \cdot 6H_2O$ (2.0818 g) dissolved in 70 mL DMF. The mixture gradually became clear and stirring was continued for 7 h to ensure complete reaction. The solution was cooled to room temperature, followed by adding methanol (16.8 mL), the mixture slowly became turbid and was stirred for 24 h at 50° C. The as-synthesized ZIF-90 particles were collected by centrifugation at 6000 rpm for 5 min and washed using 20 ml fresh methanol.

Post-Synthetic Modification of ZIF-90.

a) ZIF-92-A: (10% PSM): Parent ZIF-90 sample (100 mg, 0.39 mmol) was suspended in 10 mL methanol and ethanolamine (4.84 µL, 0.078 mmol), and refluxed at 65° C. temperature for 24 hours. The reaction mixture was cooled to room temperature, the solid was filtered and washed three times with fresh methanol (10 mL). The solid was further exchanged with fresh methanol (10 mL) for 24 h. The solid sample was dried for 24 h at 100° C. temperature.

b) ZIF-92-B: (25% PSM): Parent ZIF-90 sample (100 mg, 0.39 mmol) was suspended in 10 mL methanol and ethanolamine (12 µL, 0.196 mmol), and refluxed at 65° C. temperature for 24 hours. The reaction mixture was cooled to room temperature, the solid was filtered and washed three times with fresh methanol (10 mL). The solid was further exchanged with fresh methanol (10 mL) for 24 h. The solid sample was dried for 24 h at 100° C. temperature.

c) ZIF-92-C: (50% PSM): Parent ZIF-90 sample (100 mg, 0.39 mmol) was suspended in 10 mL methanol and ethanolamine (24 µL, 0.39 mmol), and refluxed at 65° C. temperature for 24 hours. The reaction mixture was cooled to room temperature, the solid was filtered and washed three times with fresh methanol (10 mL). The solid was further exchanged with fresh methanol (10 mL) for 24 h. The solid sample was dried for 24 h at 100° C. temperature.

d) ZIF-92-D: (75% PSM): Parent ZIF-90 sample (100 mg, 0.39 mmol) was suspended in 10 mL methanol and ethanolamine (36 µL, 0.59 mmol), and refluxed at 65° C. temperature for 24 hours. The reaction mixture was cooled to room temperature, the solid was filtered and washed three times with fresh methanol (10 mL). The solid was further exchanged with fresh methanol (10 mL) for 24 h. The solid sample was dried for 24 h at 100° C. temperature.

e) ZIF-92: (100% PSM): ZIF-92 crystals were prepared according to the procedure reported by W. Morris, C. J. Doonan, H. Furukawa, R. Banerjee and O. M. Yaghi, *Journal of the American Chemical Society,* 2008, 130, 12626-12627, incorporated herein by reference in its entirety. Briefly, dried ZIF-90 crystals (0.10 g, 0.39 mmol) were suspended in methanol (10 mL) and ethanolamine (48 µL, 0.78 mmol), and refluxed at 65° C. temperature for 24 hours. The reaction mixture was cooled to room temperature, the solid was filtered and washed three times with fresh methanol (10 mL). The solid was further exchanged with fresh methanol (10 mL) for 24 h. The solid sample was dried for 24 h at 100° C. temperature.

TABLE 1

List of reproduced and new post synthetic modified ZIF-90 materials

| ZIF name | Reference |
| --- | --- |
| ZIF-90 | Reproduced[a] |
| ZIF-92A (10% PSM-ZIF-90) | This work |
| ZIF-92B (25% PSM-ZIF-90) | This work |
| ZIF-92C (50% PSM-ZIF-90) | This work |
| ZIF-92D (75% PSM-ZIF-90) | This work |
| ZIF-92 (100% PSM-ZIF-90) | Reproduced[a] |

[a]W. Morris, C. J. Doonan, H. Furukawa, R. Banerjee and O. M. Yaghi, *Journal of the American Chemical Society*, 2008, 130, 12626-12627, incorporated herein by reference in its entirety Results and Discussion To improve material performance, the accessible window diameter of a ZIF filler was modified using post-synthetic modification (PSM) to control the gas transport properties. These modifications were carried out using single and tandem modification steps for the rational enhancement of $CO_2$ affinity and selectivity for the synthesis of new ZIFs of sodalite topology. Different preparation procedures have been explored in order to improve yield and phase purity, and nucleation at 80° C. was found to give the highest yield with no compromising of the phase purity as shown by powder X-ray diffraction (PXRD, FIG. 3). The resulting particles have uniform polyhedron morphology with narrow dispersity (10 µm particle size) as exhibited from scanning electron microscopy images (SEM, FIG. 4A).

Figure 10A:
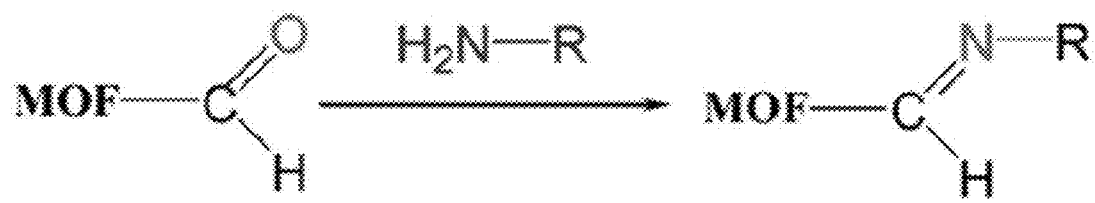
FIGS. 10A-10B illustrate an imine condensation reaction (FIG. 10A) and a schematic model for ZIF-90 functionalization with ethanolamine to form PSM-ZIF-90.
Figure 10B:
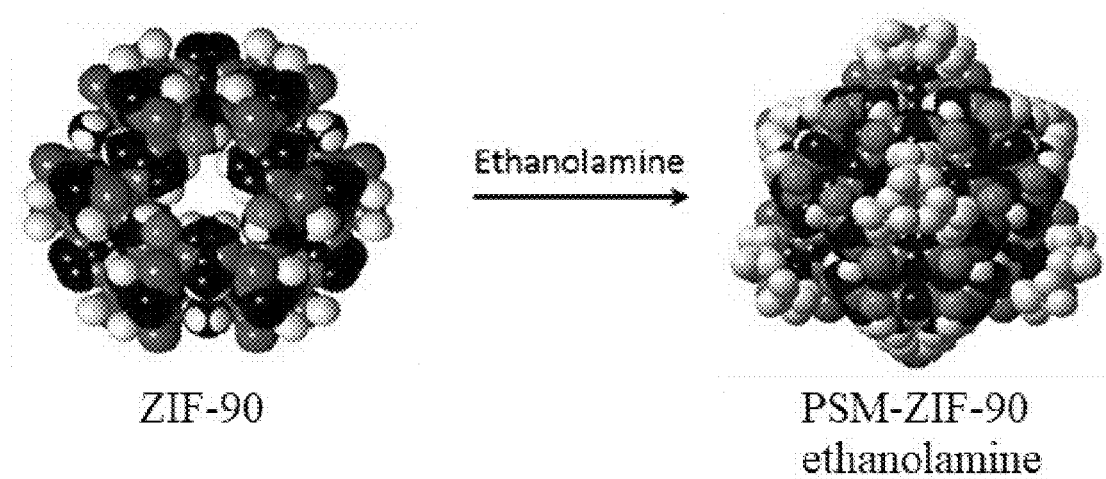

In order to perform the post-synthetic modification, an imine condensation reaction of the aldehyde and ethanolamine (through amine functionality) was carried out in methanol at 65° C. with stirring for 24 hours (FIGS. 10A-10B).

Figure 3:
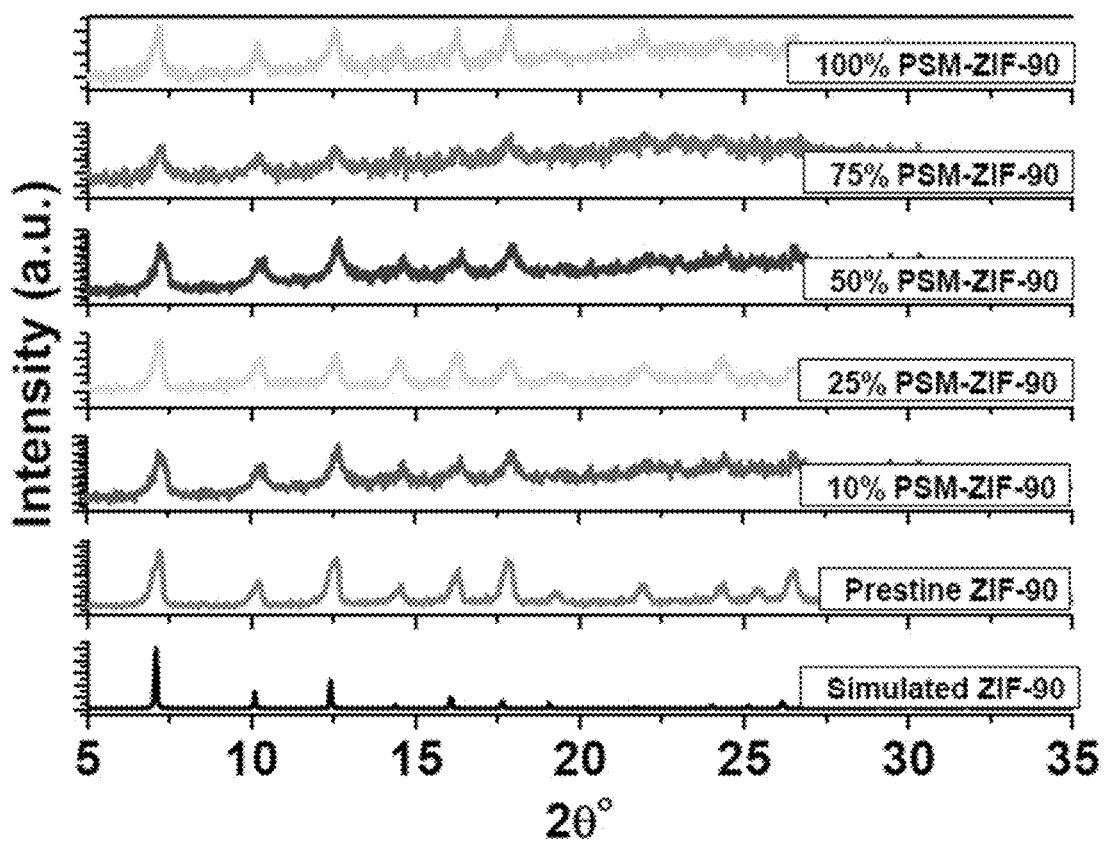
FIG. 3 illustrates PXRD patterns of the simulated ZIF-90, parent (pristine) ZIF-90, ZIF-92A (10% PSM-ZIF-90), ZIF-92B (25% PSM-ZIF-90), ZIF-92C (50% PSM-ZIF-90), ZIF-92D (75% PSM-ZIF-90), and ZIF-92 (100% PSM-ZIF-90)
Figure 4A:
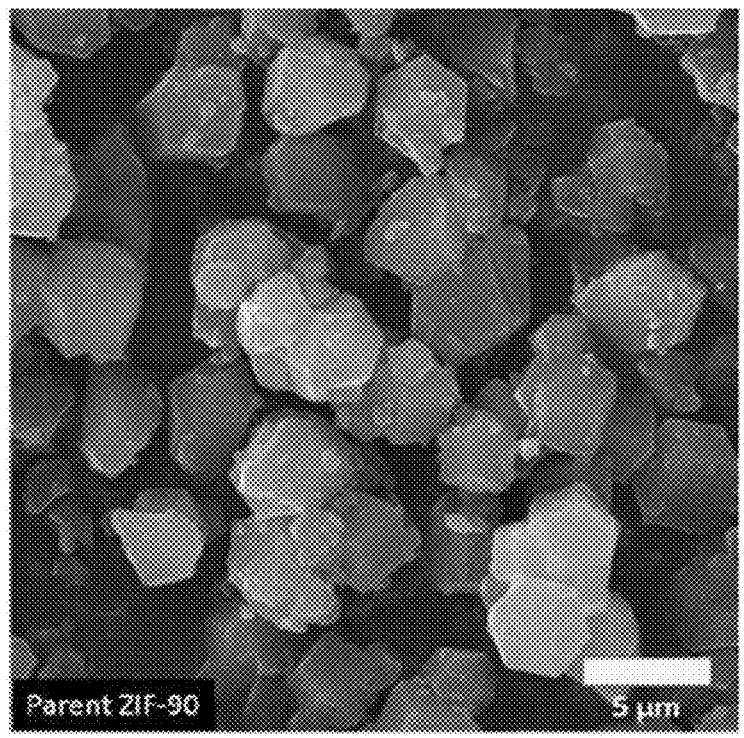
FIGS. 4A-4D illustrate scanning electron microscopy (SEM) images of ZIF-90 (FIG. 4A), ZIF-92B (FIG. 4B), ZIF-92D (FIG. 4C), and ZIF-92 (FIG. 4D), where the morphology of each PSM material remained stable.
Figure 4B:
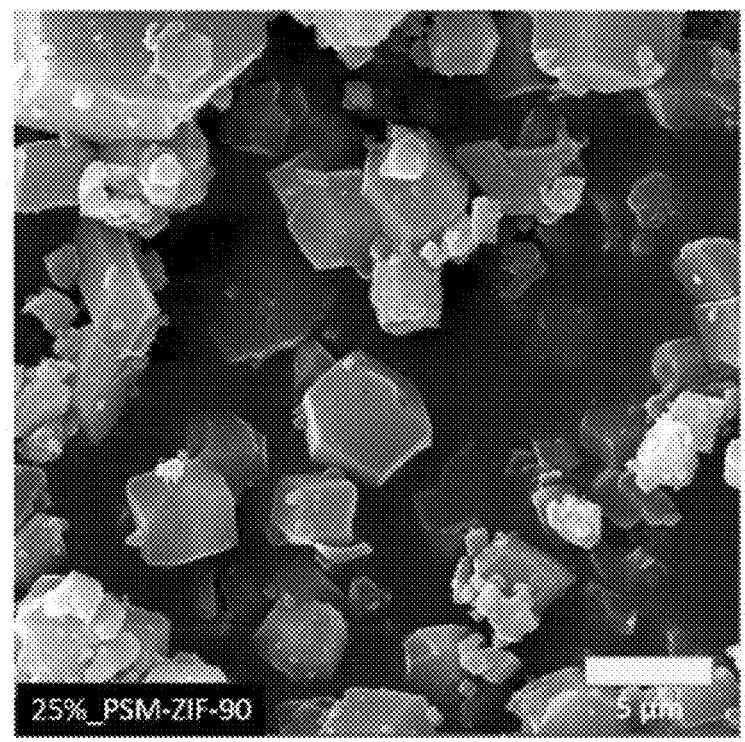
Figure 4C:
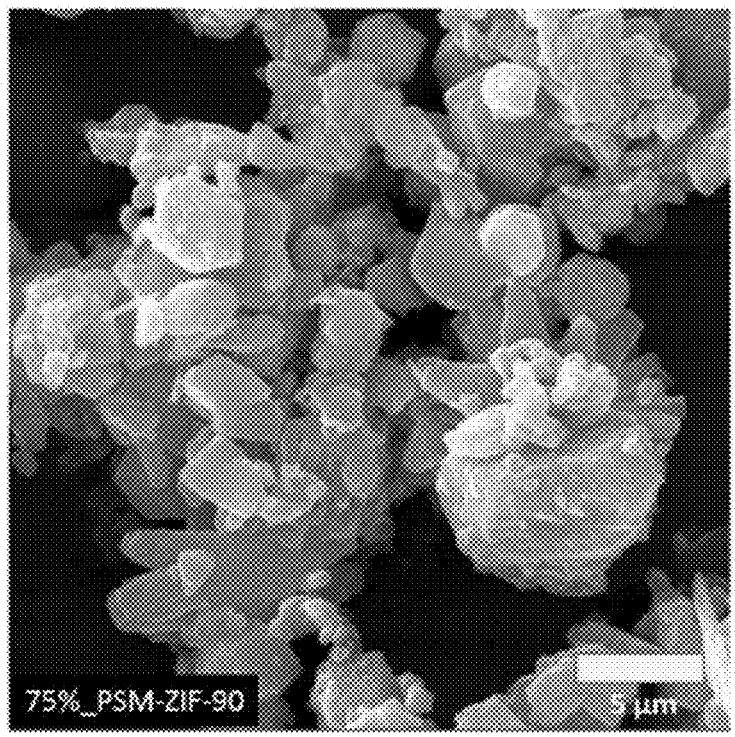
Figure 4D:
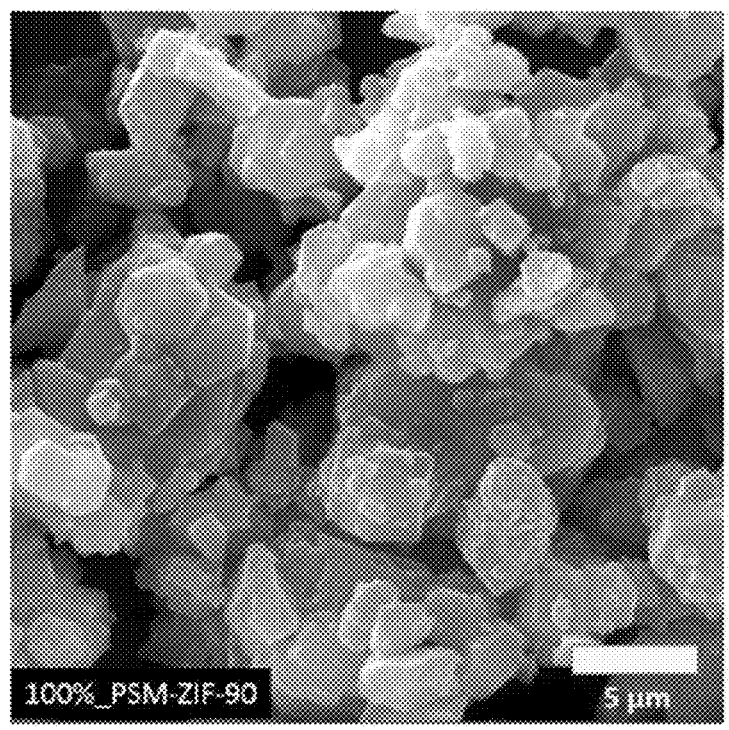

The resulting powder was collected, and washed with methanol. ZIF-90 functionalization was associated with some distortion of morphology (FIGS. 4B-4D), but the structure is retained as depicted from PXRD patterns, which showed an excellent match between the simulated and the experimental patterns (FIG. 3).

Figure 5A:
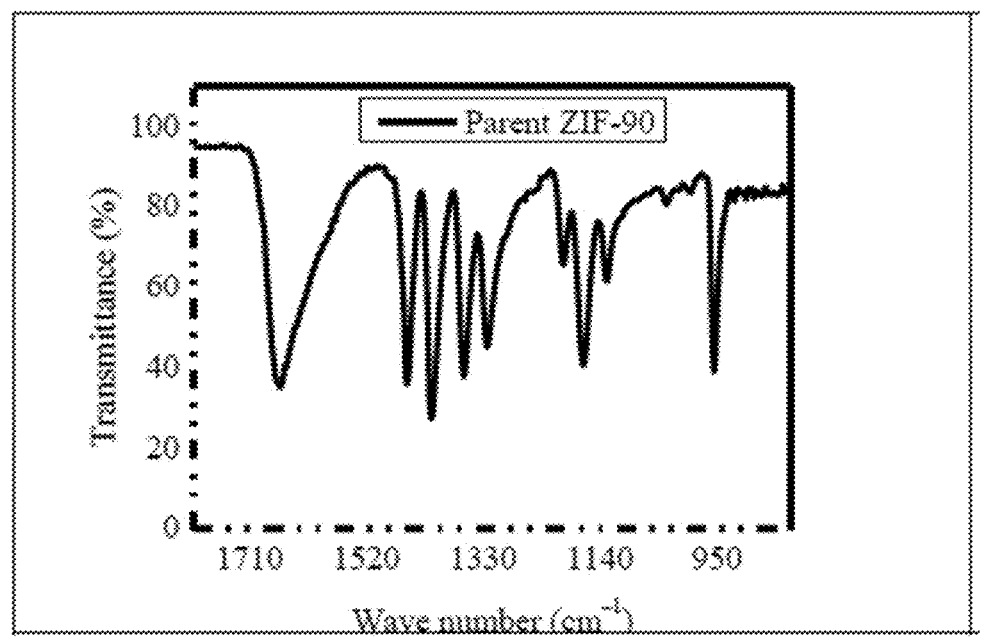
FIGS. 5A-5B show the infrared (FT-IR) spectra of ZIF-90, with FIG. 5B being an expanded view of the carbonyl/imine region.
Figure 5B:
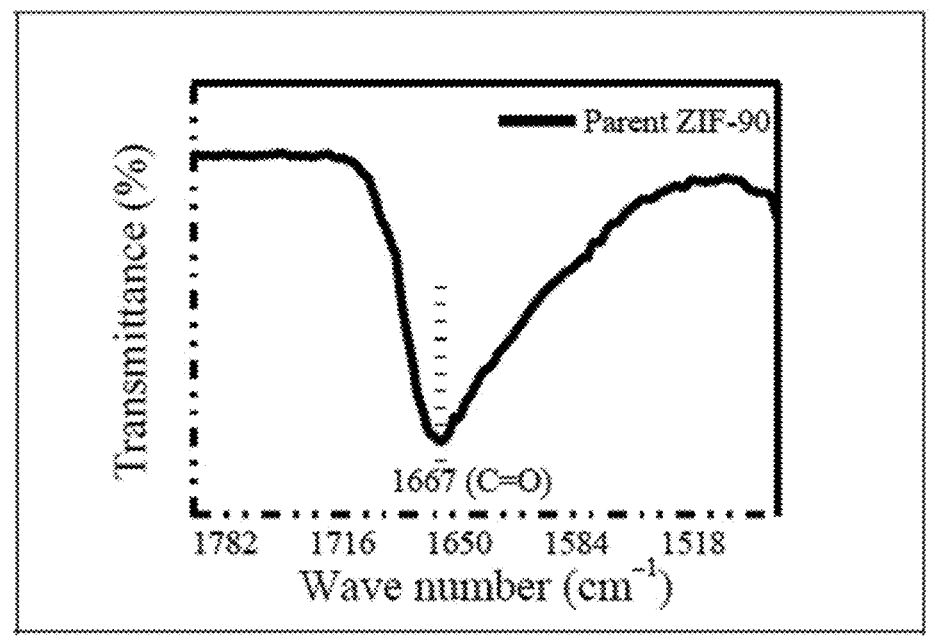
Figure 5C:
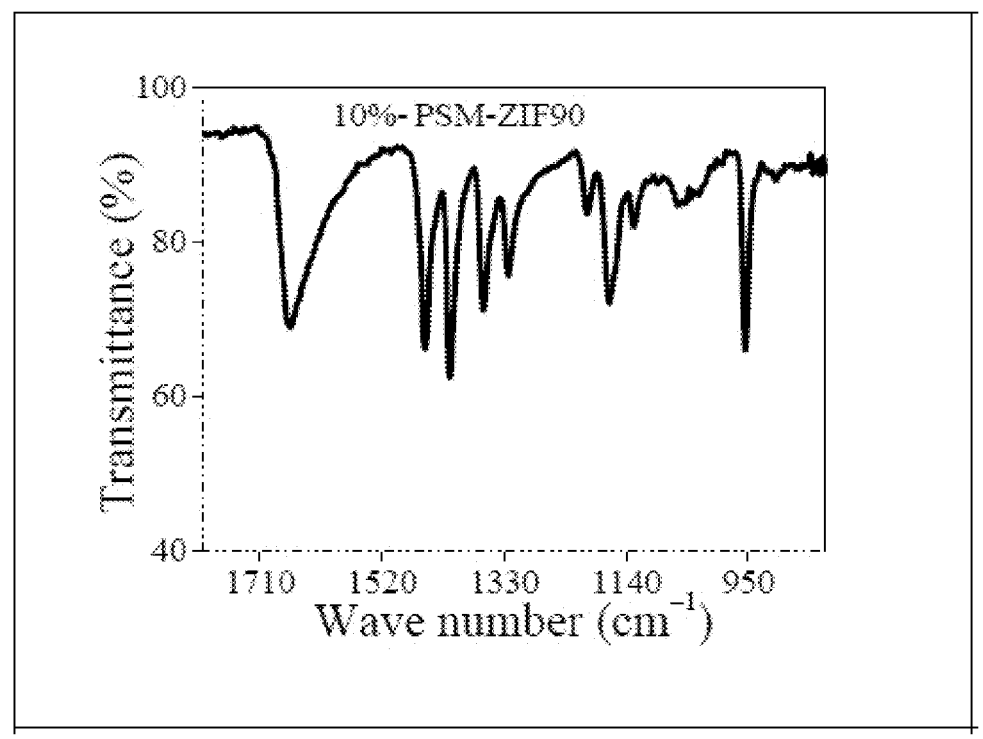
FIGS. 5C-5D show the infrared (FT-IR) spectra of ZIF-92A (10% PSM-ZIF-90), with FIG. 5D being an expanded view of the carbonyl/imine region.
Figure 5D:
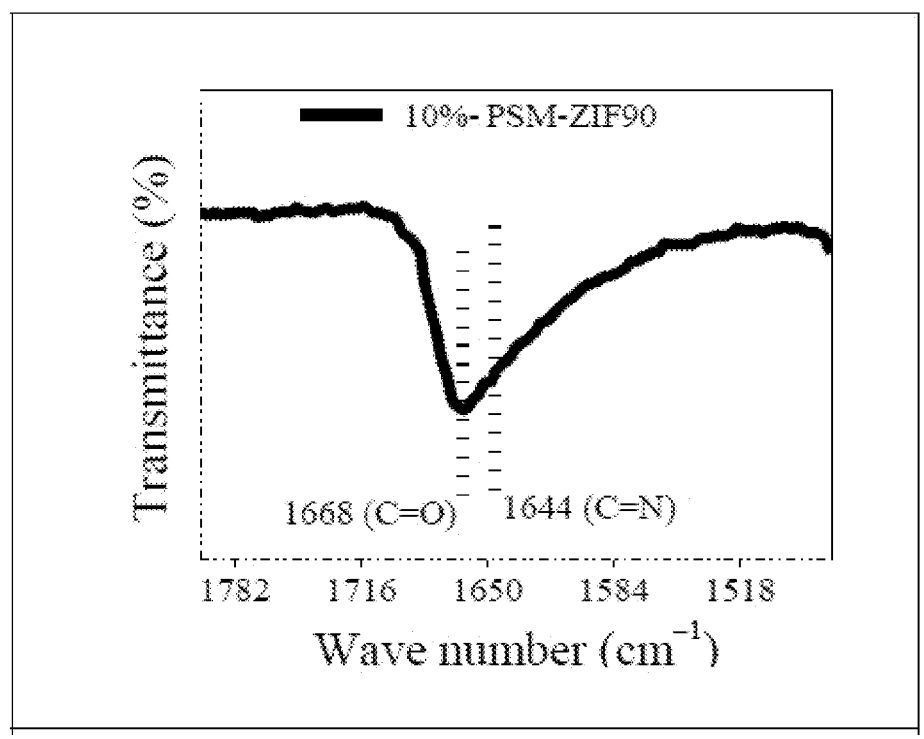
Figure 5E:
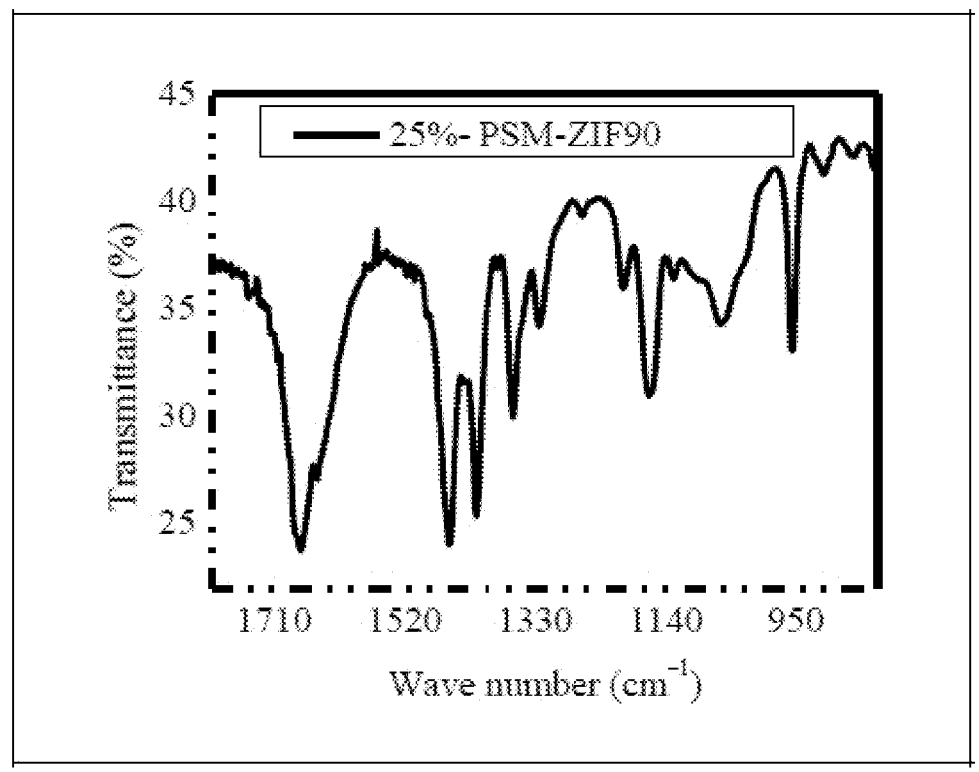
FIGS. 5E-5F show the infrared (FT-IR) spectra of ZIF-92B (25% PSM-ZIF-90), with FIG. 5F being an expanded view of the carbonyl/imine region.
Figure 5F:
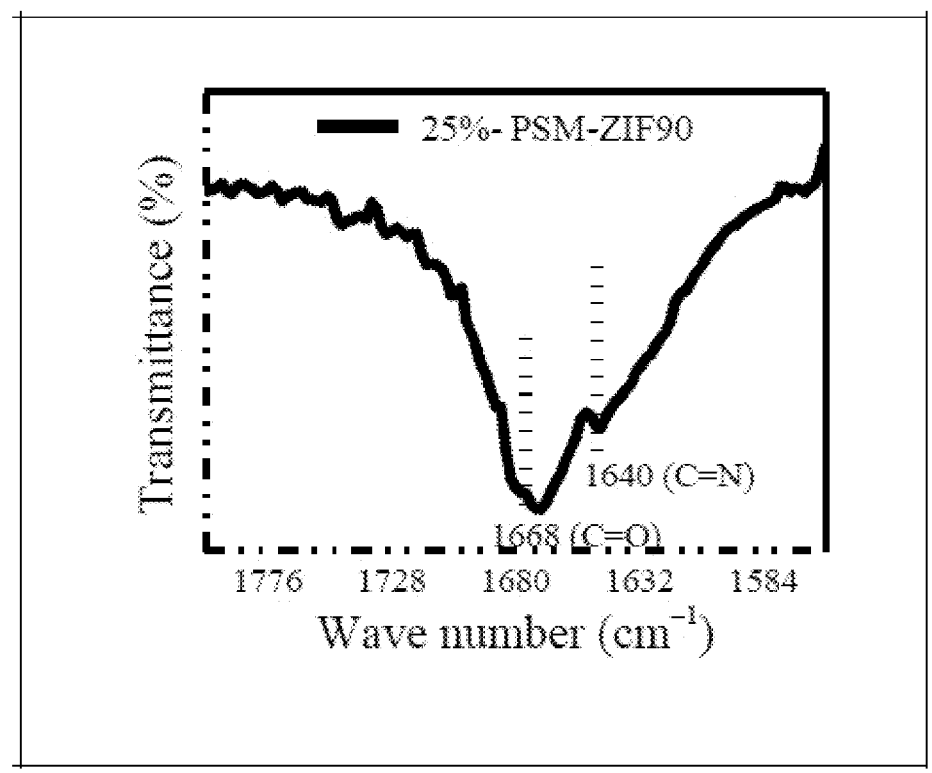
Figure 5G:
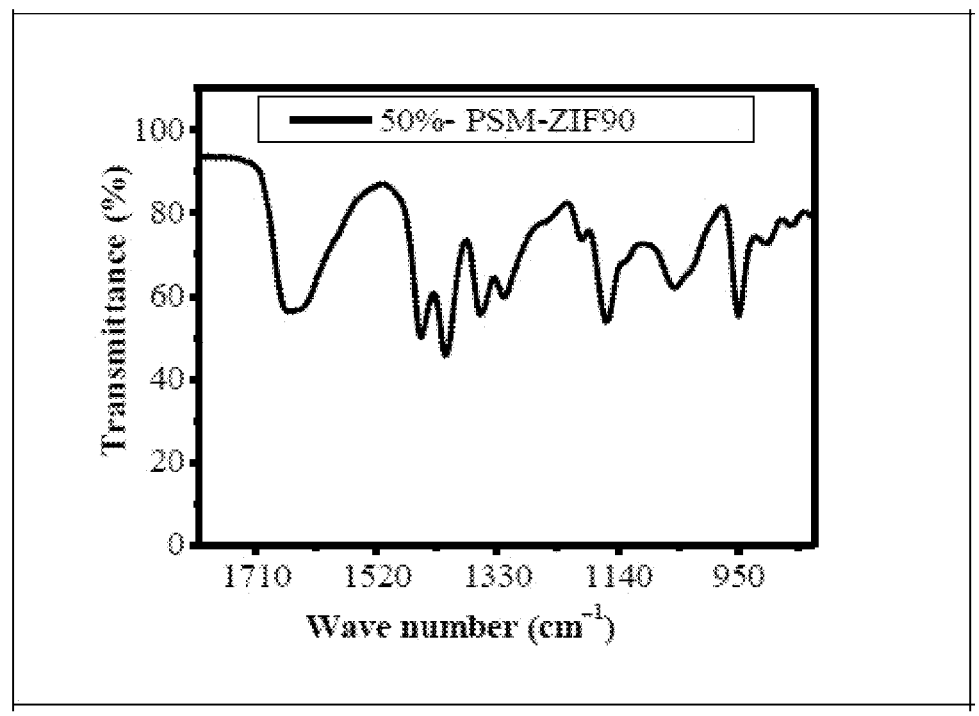
FIGS. 5G-5H show the infrared (FT-IR) spectra of ZIF-92C (50% PSM-ZIF-90), with FIG. 5H being an expanded view of the carbonyl/imine region.
Figure 5H:
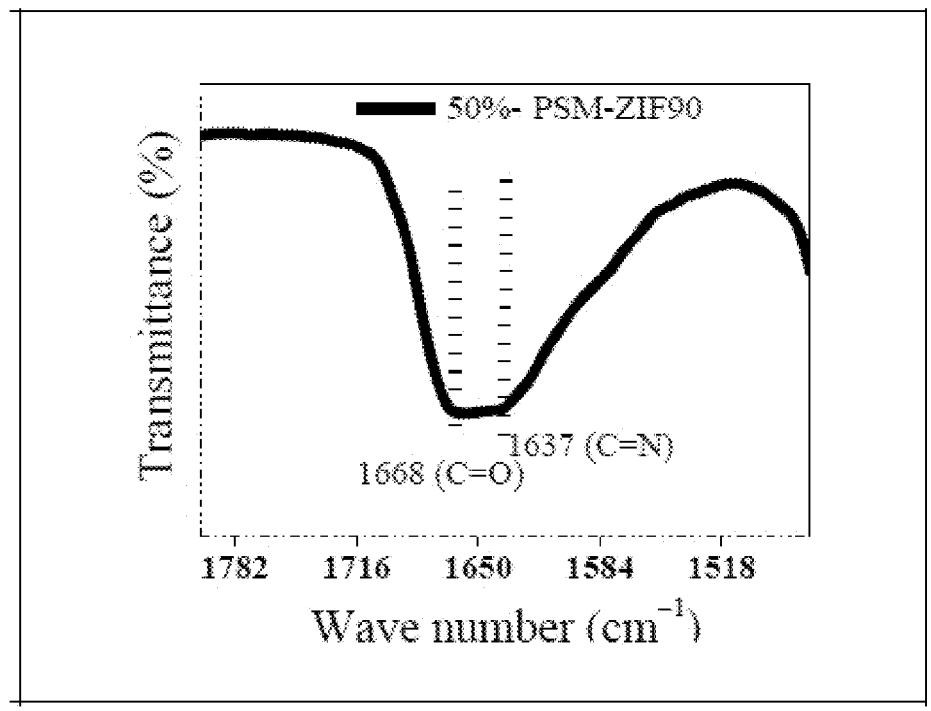
Figure 5I:
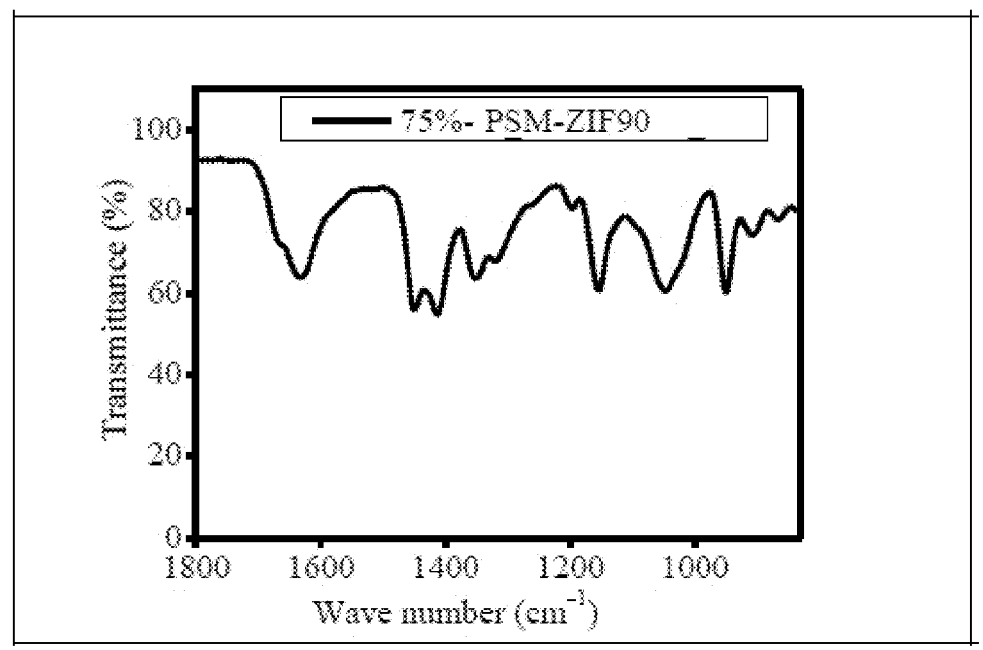
FIGS. 5I-5J show the infrared (FT-IR) spectra of ZIF-92D (75% PSM-ZIF-90), with FIG. 5J being an expanded view of the carbonyl/imine region.
Figure 5J:
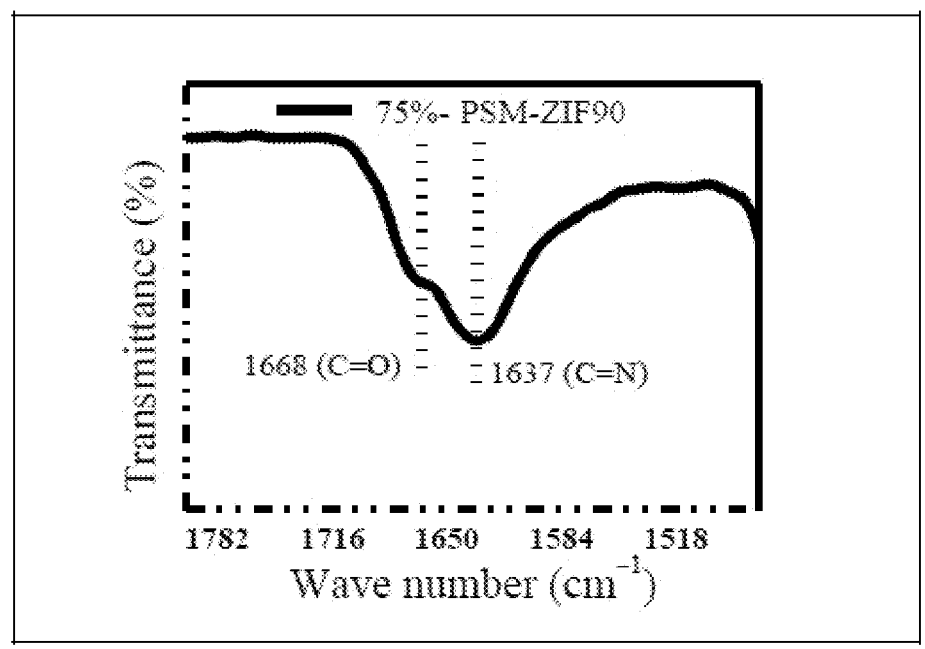
Figure 5K:
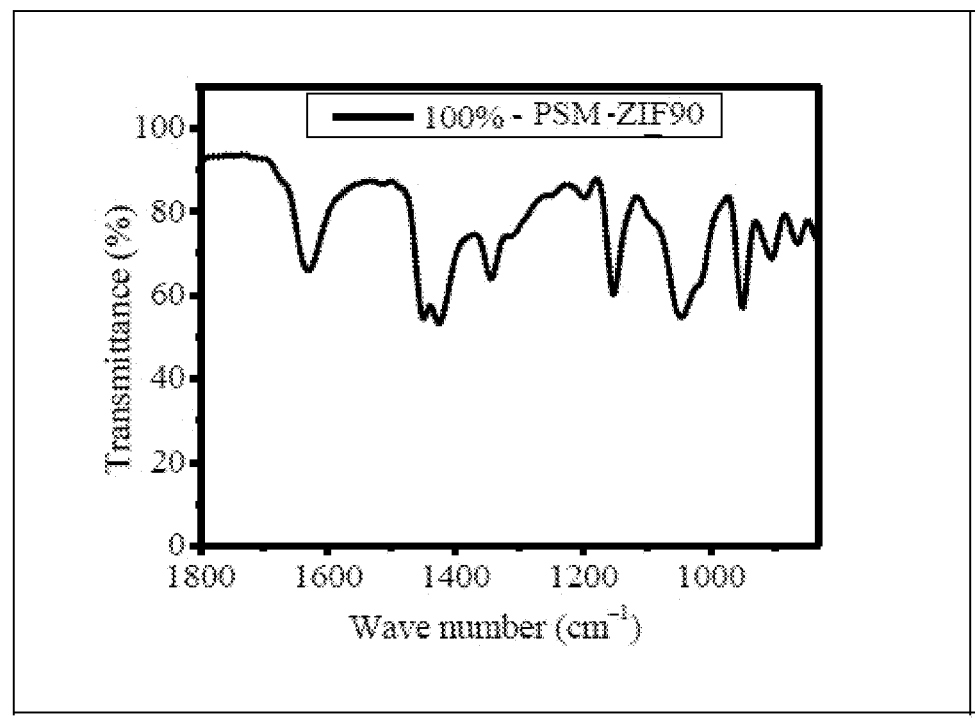
FIGS. 5K-5L show the infrared (FT-IR) spectra of ZIF-92 (100% PSM-ZIF-90), with FIG. 5L being an expanded view of the carbonyl/imine region.
Figure 5L:
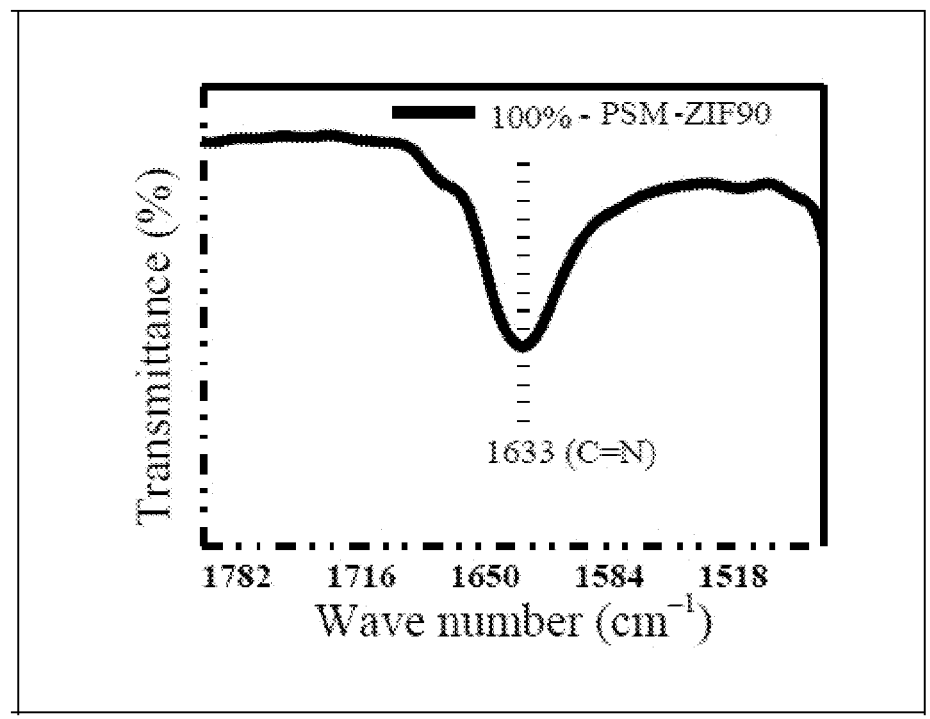

Infrared (FTIR) spectra were collected for the different products to track the extent of imine functionality formation compared with ZIF-90. The absorption band at 1668 $cm^{-1}$ corresponding to the C=O stretching was found to be diminishing with further functionalization, which was associated with the appearance of a band at 1637 $cm^{-1}$ that is characteristic for imine (C=N) bond stretching. See W. Morris, C. J. Doonan and O. M. Yaghi, *Inorg Chem,* 2011, 50, 6853-6855, incorporated herein by reference in its entirety. This signal was proportional to the degree of functionalization, as shown by FIGS. 5A-5L. Further characterization was carried out by 1H NMR to confirm the degree of functionalization (FIG. 5M).

Figure 6D:
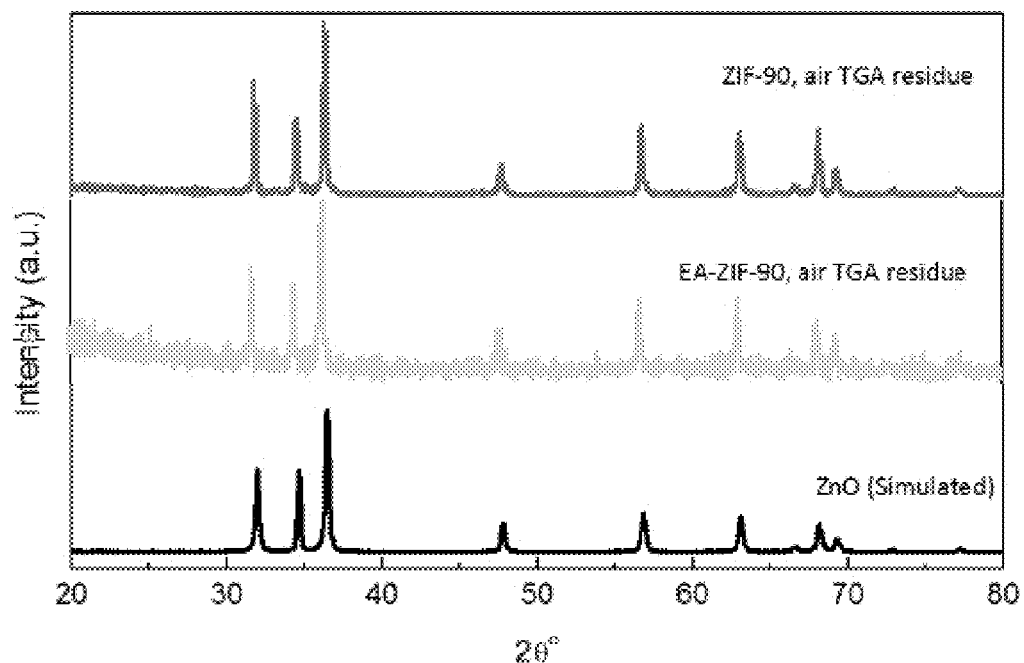
FIG. 6D shows the PXRD analysis of the TGA residue result from heating ZIF-90 and PSM-ZIF-90 that is comparable to the pattern of ZnO simulated from single crystal structure.

Thermal gravimetric analysis was carried out on and compared to the ZIF-90. The ethanolamine functionalized ZIF-90 material that showed a weight loss at 150° C. that can be attributed to the ethanolamine dissociation (FIGS. 6A-6C) and the residue was analyzed by PXRD and confirmed the formation of the ZnO residue from the heating treatment of the ZIF materials under air stream (FIG. 6D). The lower ZnO residue on the functionalized ZIF-90 is a result of the higher organic content generated from the ZIF-90 functionalization that dissociates upon thermal treatment in the presence of oxygen.

Figure 7:
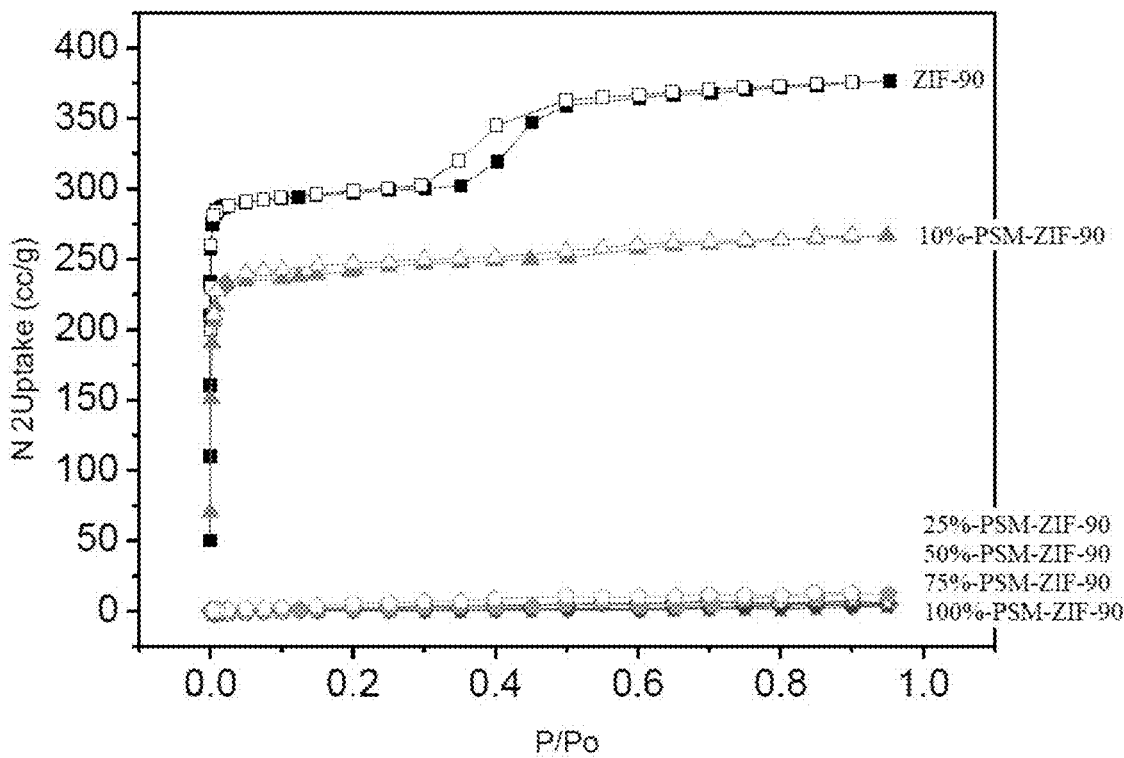
FIG. 7 is a graph illustrating the $N_2$ adsorption isotherms of ZIF-90 and different samples of the PSM-ZIF-90 at 77 K. Filled and open symbols represent adsorption and desorption branches, respectively.
Figure 8A:
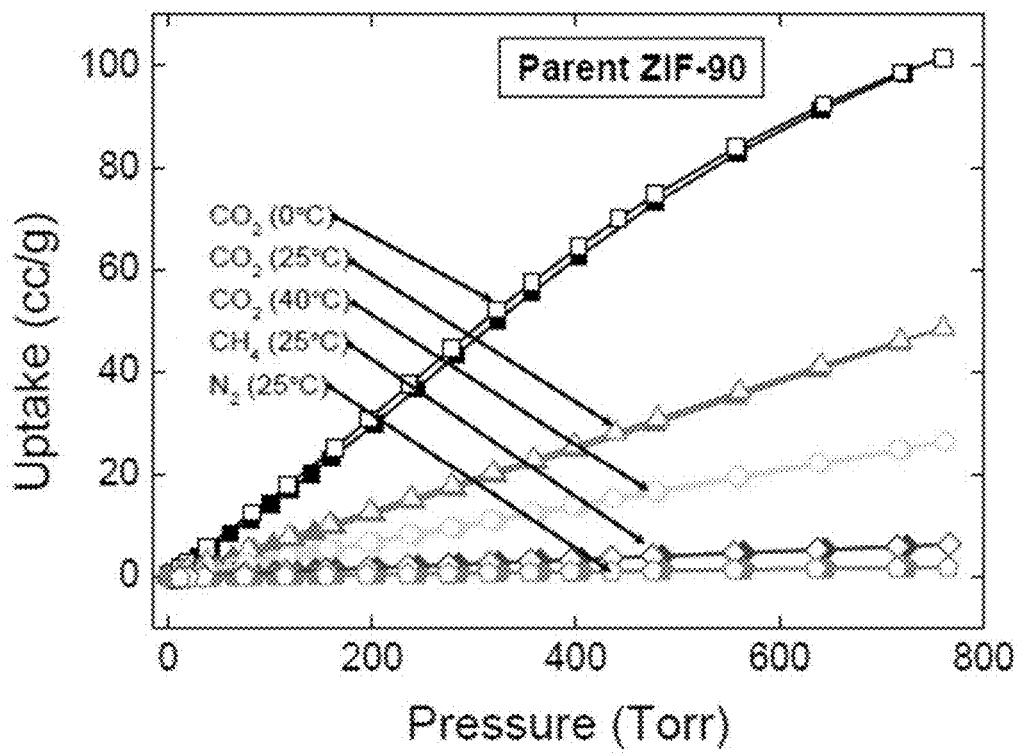
FIGS. 8A-8F are graphs illustrating the isotherms for $CO_2$ at 273K (squares), $CO_2$ at 298K (triangles), $CO_2$ at 313K (circles), $CH_4$ at 298 K (diamond) and $N_2$ at 298 K (pentagons) for ZIF-90 (FIG. 8A), 10% PSM-ZIF-90 (FIG. 8B), 25% PSM-ZIF-90 (FIG. 8C), 50% PSM-ZIF-90 (FIG. 8D), 75% PSM-ZIF-90 (FIG. 8E), 100% PSM-ZIF-90 (FIG. 8F), where filled and open symbols represent adsorption and desorption branches, respectively.
Figure 8B:
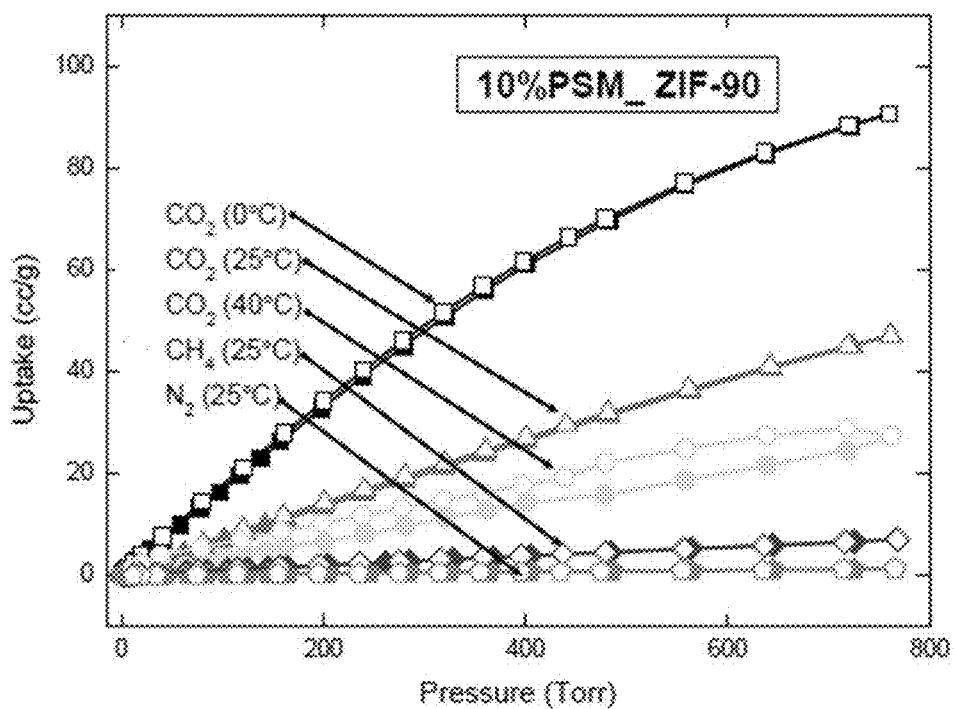
Figure 8C:
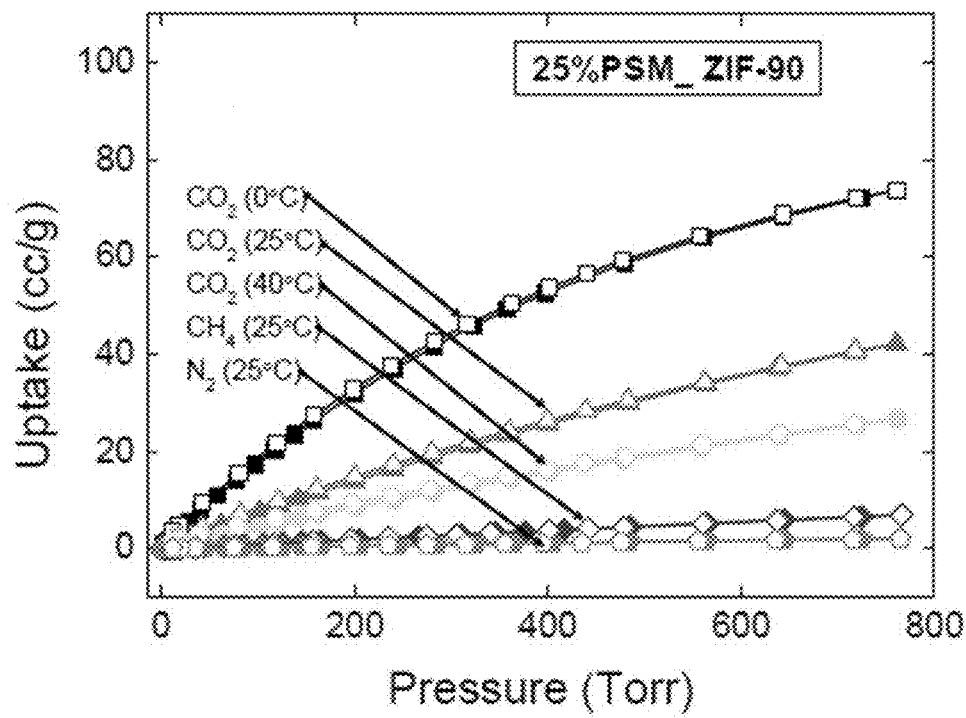
Figure 8D:
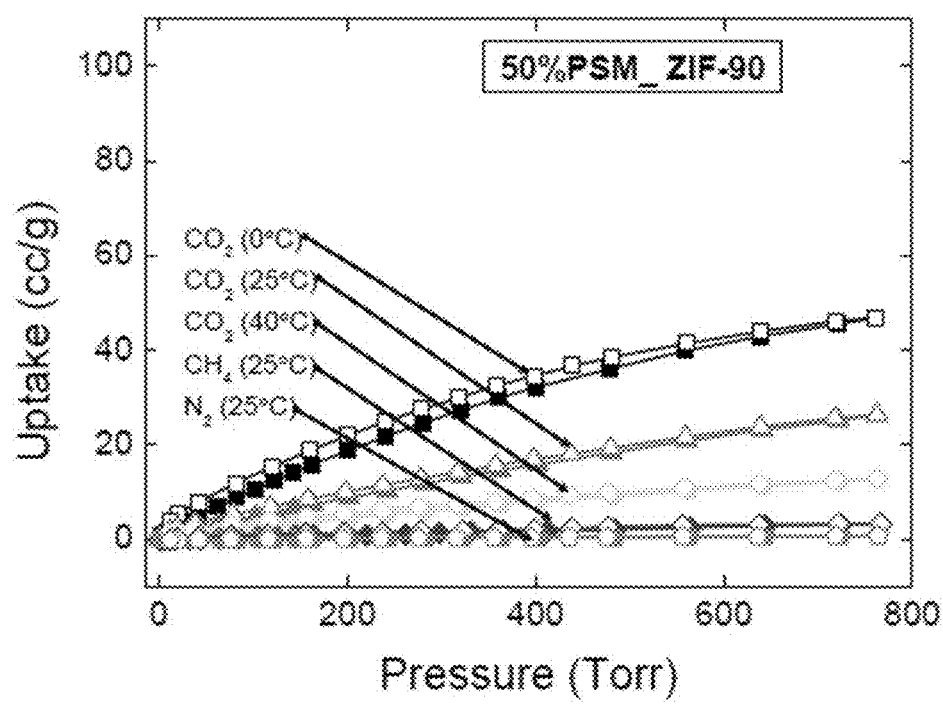
Figure 8E:
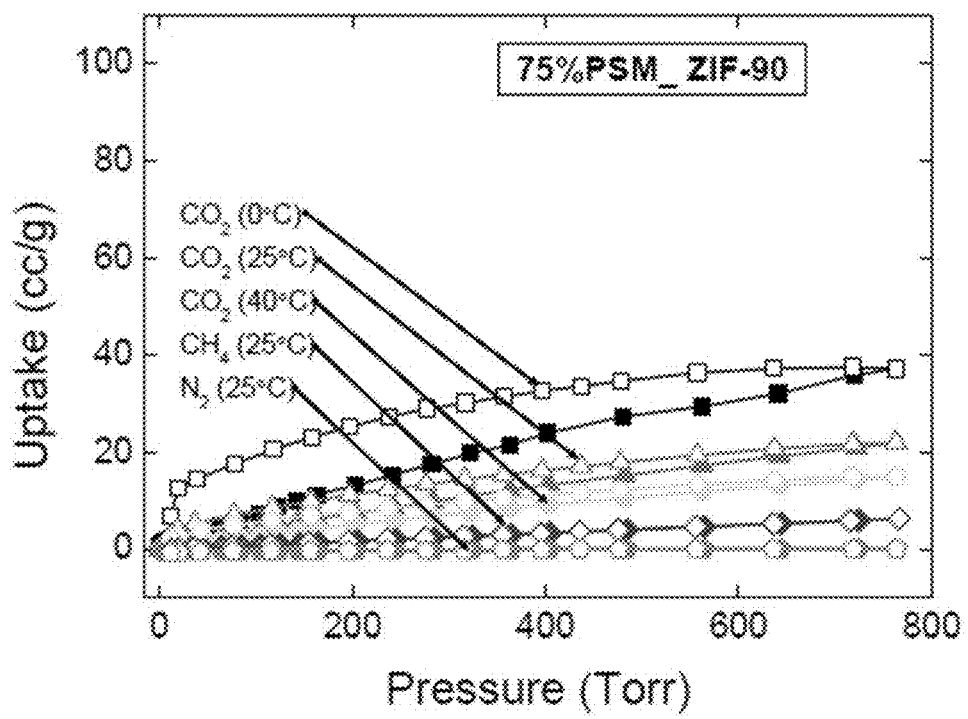
Figure 8F:
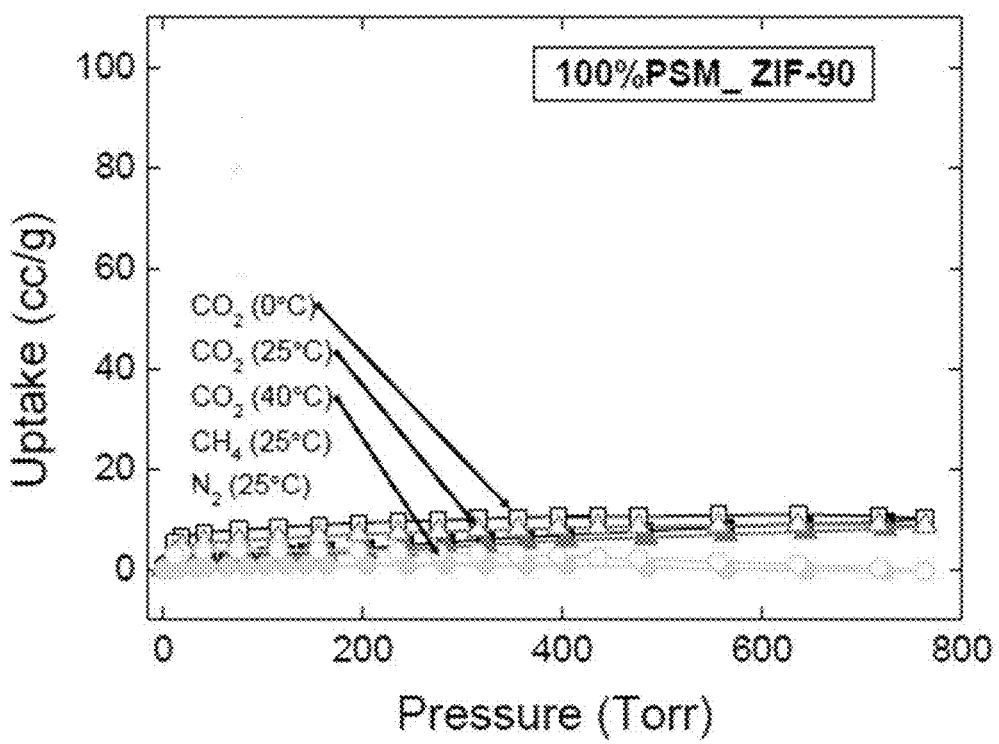
Figure 9A:
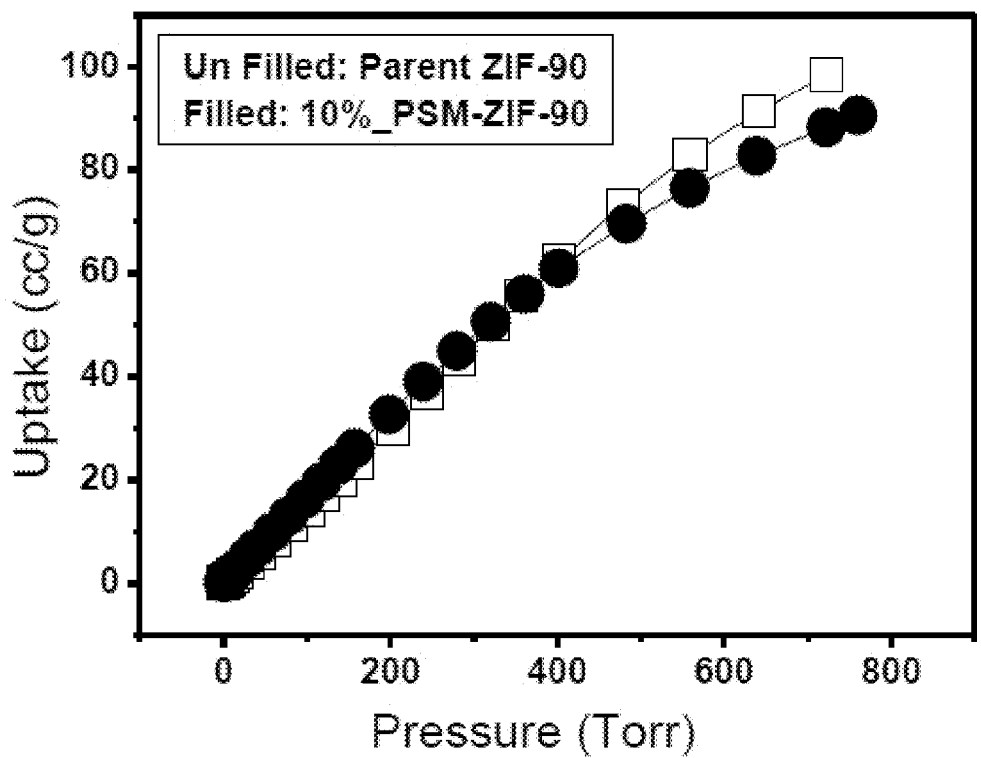
FIGS. 9A-9J illustrate a comparison of the adsorption isotherms of $CO_2$ for ZIF-90 (open squares) to each of ZIF-92A (10% PSM-ZIF-90), ZIF-92B (25% PSM-ZIF-90), ZIF-92C (50% PSM-ZIF-90), ZIF-92D (75% PSM-ZIF-90), and ZIF-92 (100% PSM-ZIF-90), each represented by filled circles at 273K, with each isotherm also shown in expanded form in a low pressure region of 0-200 Torr.
Figure 9B:
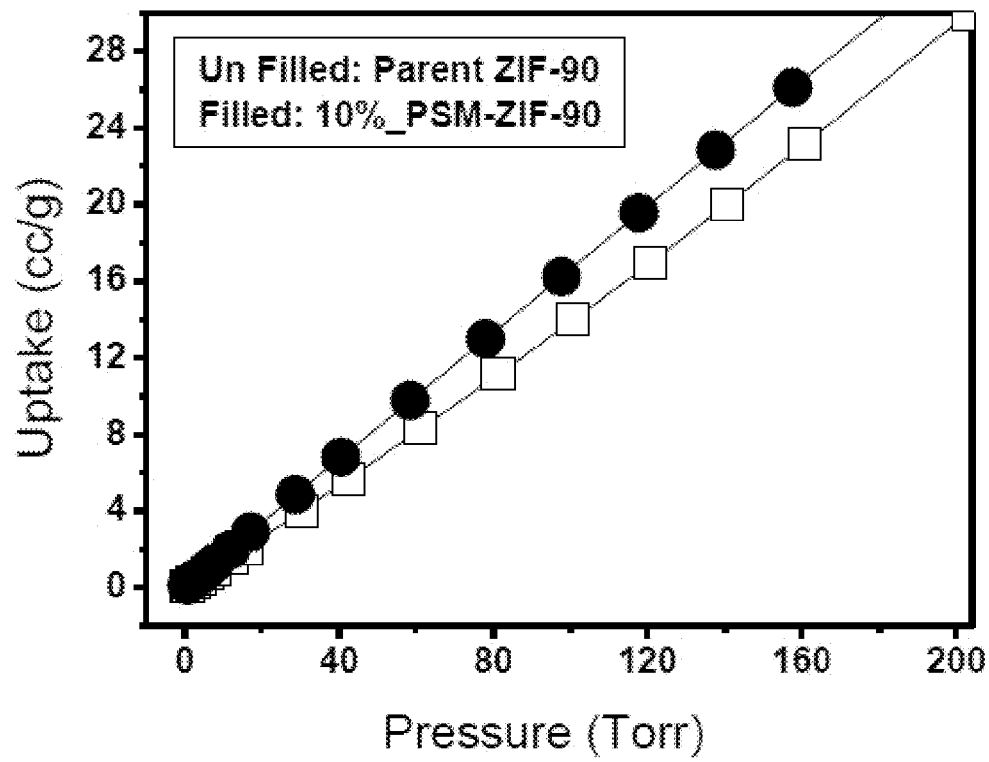
Figure 9C:
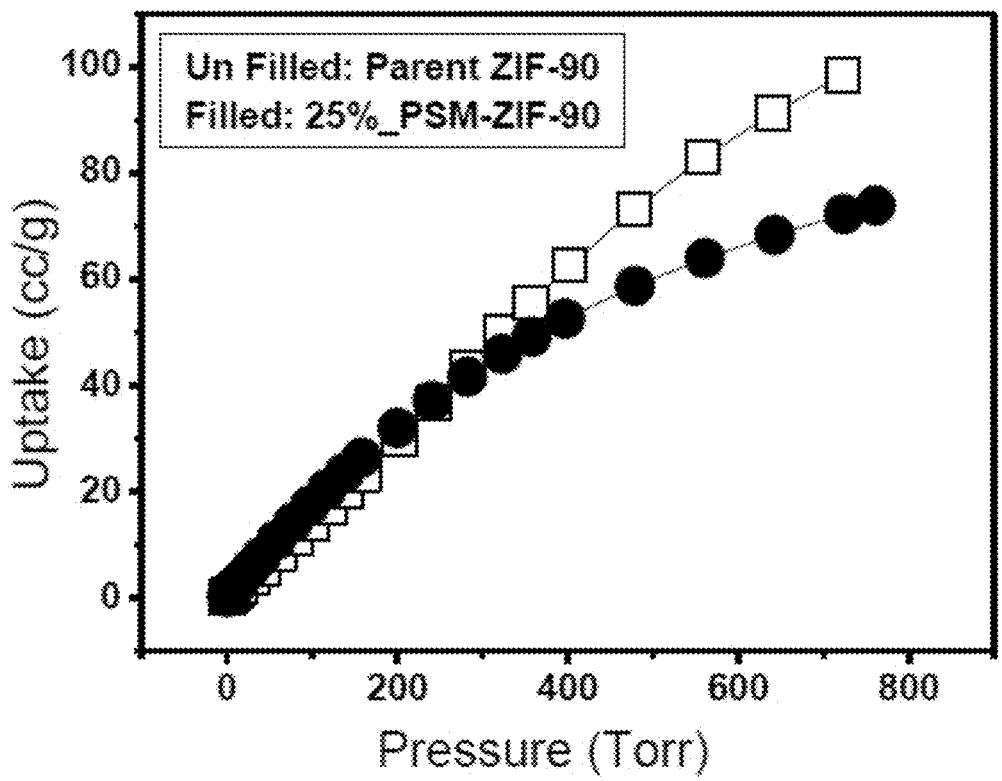
Figure 9D:
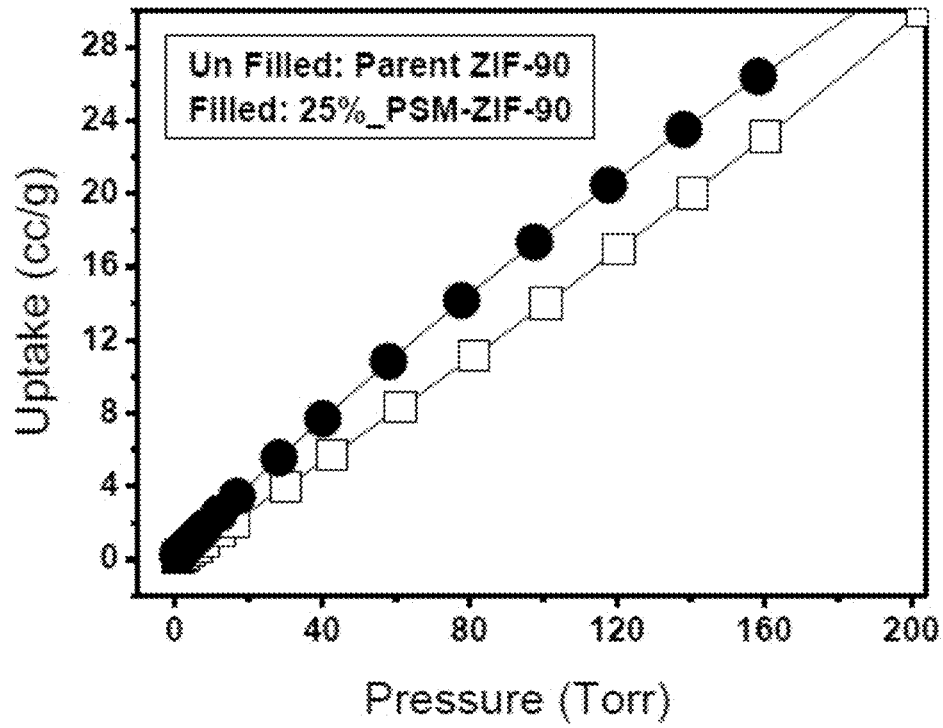
Figure 9E:
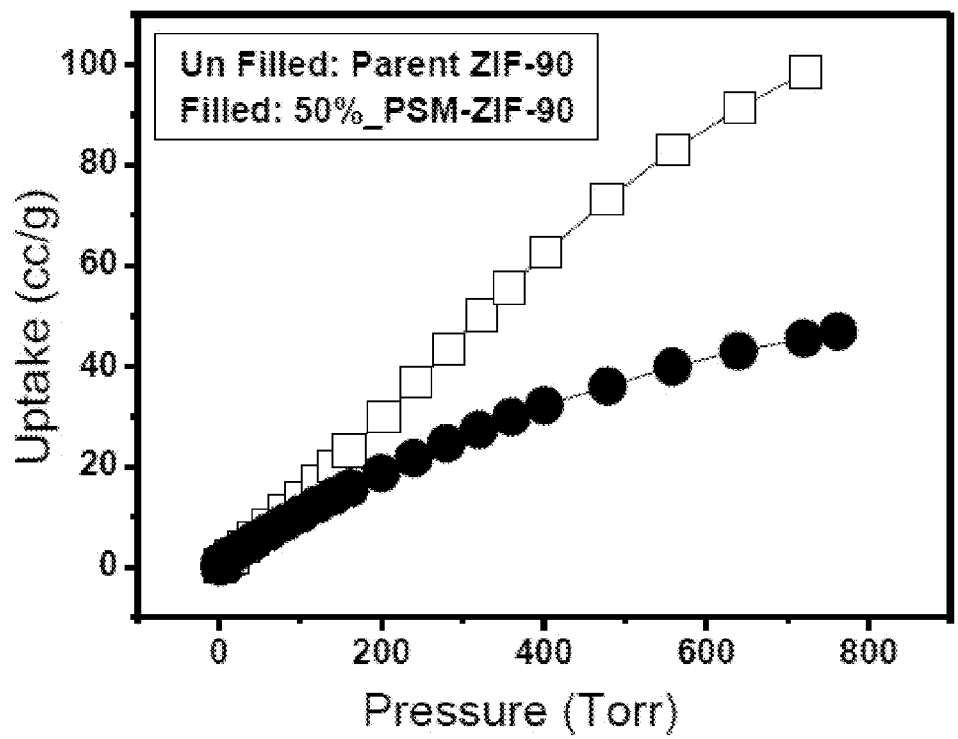
Figure 9F:
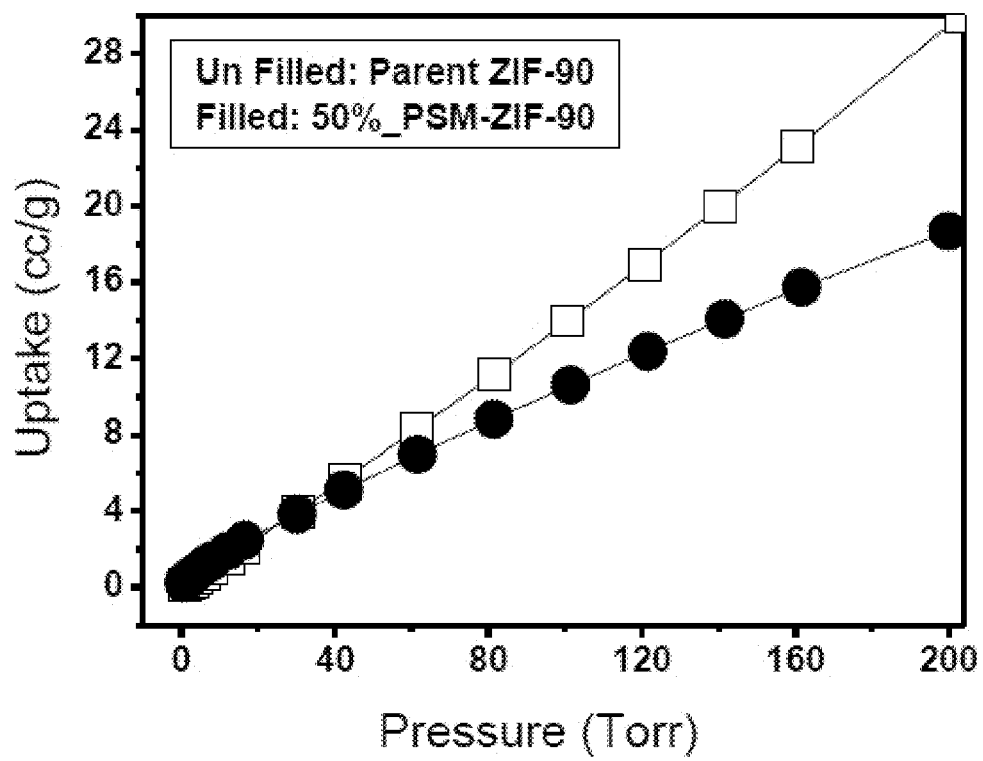
Figure 9G:
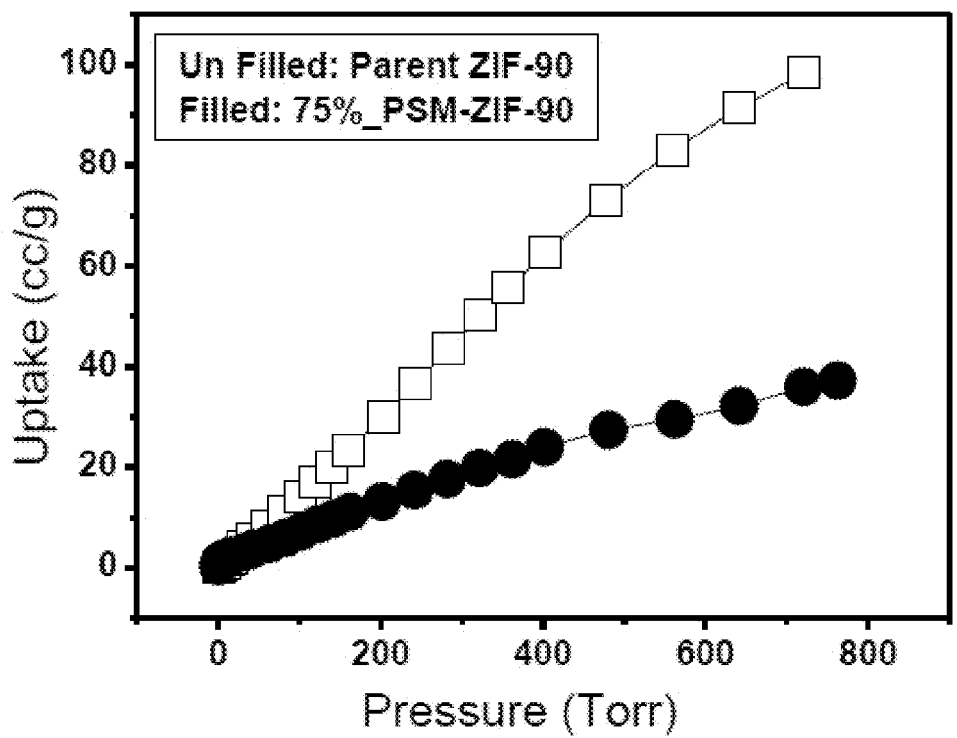
Figure 9H:
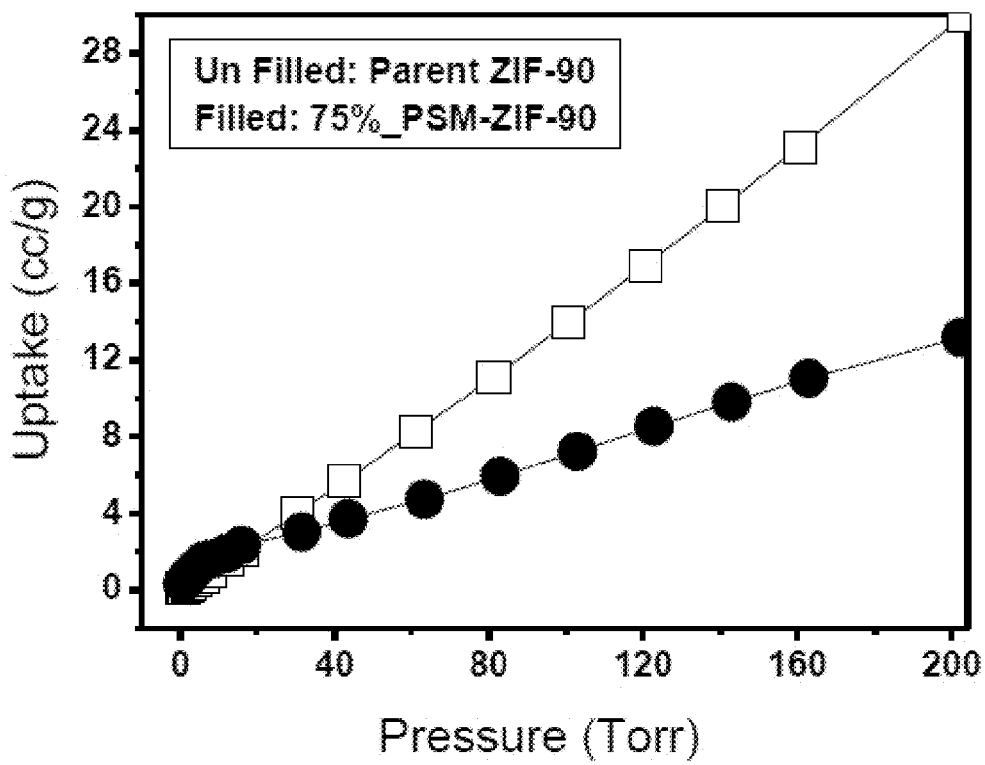
Figure 9I:
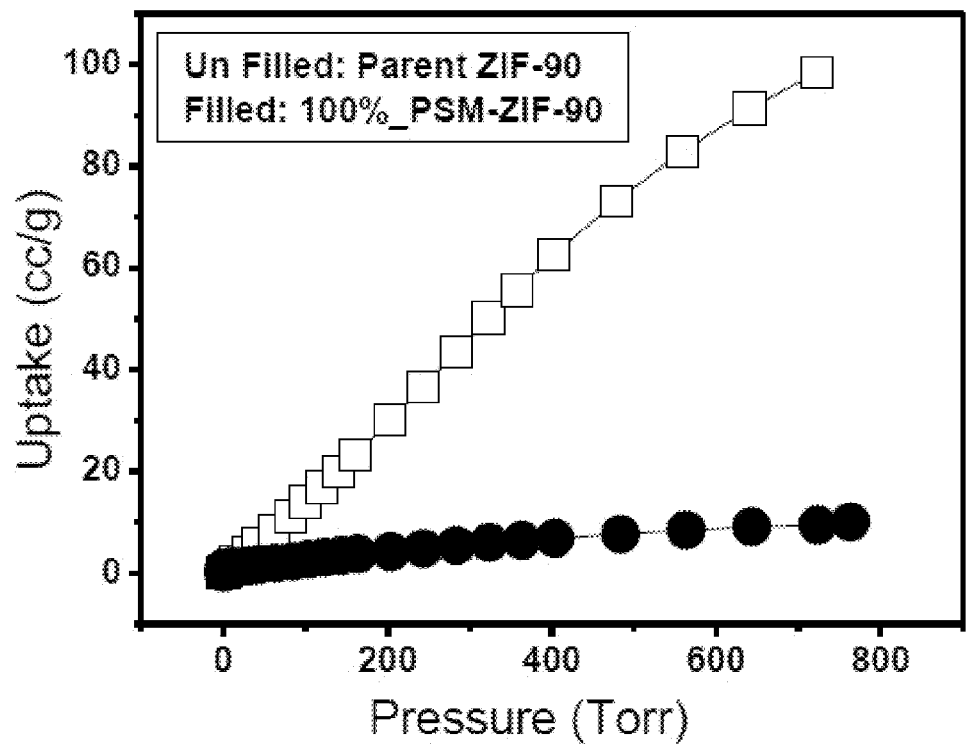
Figure 9J:
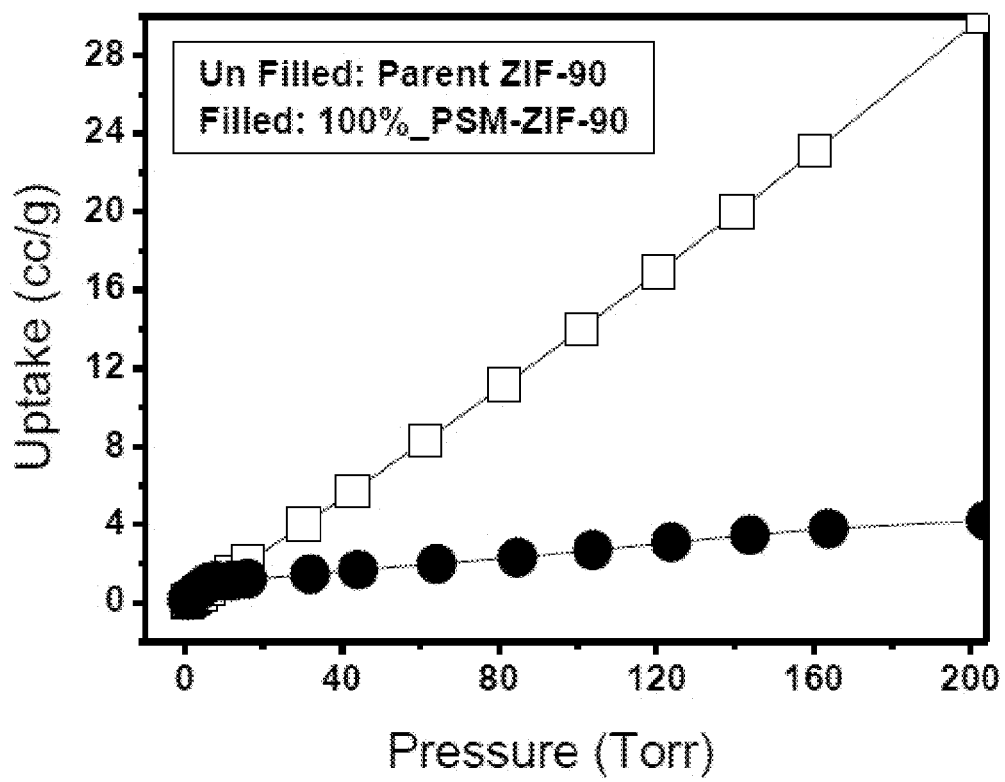

Brunauer-Emmett-Teller (BET) and Langmuir surface areas of the prepared ZIF-90 was 1235 comparable to the reported 1320 $m^2g^{-1}$ calculated from the $N_2$ isotherm at 77 K. See W. Morris, C. J. Doonan, H. Furukawa, R. Banerjee and O. M. Yaghi, *Journal of the American Chemical Society,* 2008, 130, 12626-12627, incorporated herein by reference in its entirety. Notably, the $N_2$ isotherms of ZIF-92-B, ZIF-92-C, ZIF-92-D, and ZIF-92 (100% PSM) show a minor $N_2$ uptake, which might be the result of the blocking of the ZIF-90 framework by the resulting functionality at the ZIF-90 window, which prevents $N_2$ molecules from accessing the interior of the pores (FIG. 7).

On the basis of the ZIF-90 and PSM-ZIF-90 structures, controlled porosity and thermal stability, the thermodynamic gas adsorption properties of the prepared materials were evaluated. Accordingly, low-pressure, single-component gas adsorption isotherms for $CO_2$ capture were measured on parent ZIF-90 and newly synthesized PSM-ZIF-90s at 273, 298 and 313 K up to 760 Torr as shown in FIGS. 8A-8F and summarized in Table 2. ZIF-90 was found to have the highest $CO_2$ uptake and the total uptake decreases with the increase of PSM with ethanolamine. But, it is noteworthy that 10% PSM-ZIF-90 (ZIF-92A) and 25% PSM-ZIF-90 (ZIF-92B) at a low pressure region showed higher uptake than the parent ZIF-90 (FIGS. 9A-9D) which demonstrates the potential use of these materials for practical $CO_2$ capture and separation. The selectivity of $CO_2/N_2$ and $CO_2/CH_4$ were calculated using single component isotherms by Henry's law and summarized in Table 3. Consistent with the $N_2$ isotherms the selectivities of $CO_2/N_2$ and $CO_2/CH_4$ were found to increases with the increase in PSM. The highest selectivities were observed in 75% PSM-ZIF-90. This is due to the restricted pore window for $N_2$ and $CH_4$ but high $CO_2$ affinity towards $CO_2$ due to imines. This observation indicates the stronger $CO_2$ interactions (i.e. higher affinity) than is found for $N_2$ and $CH_4$ which lends credence to the potential of this material to serve as an adsorbent for selective $CO_2$ capture from flue gas.

TABLE 2

Carbon dioxide capture by ZIF-90 and PSM-ZIF-90s

| ZIF name | Capacity (cc/g) 273 K | Capacity (cc/g) 293 K | Pressure (bar) | Reference |
|---|---|---|---|---|
| ZIF-90 | 98.44 | 48.57 | 1 | This work |
| ZIF-92A (10% PSM-ZIF-90) | 90.58 | 46.97 | 1 | This work |
| ZIF-92B (25% PSM-ZIF-90) | 73.87 | 42.2 | 1 | This work |
| ZIF-92C (50% PSM-ZIF-90) | 46.87 | 26.25 | 1 | This work |
| ZIF-92D (75% PSM-ZIF-90) | 37.21 | 22.01 | 1 | This work |
| ZIF-92 (100% PSM-ZIF-90) | 10.04 | 8.63 | 1 | This work |
| ZIF-90 | — | 47.04 (simulated) | 1 (simulated) | Hu et al.[a] |

[a] J. Hu, Y. Liu, J. Liu and C. Gu, *Fuel*, 2017, 200, 244-251, incorporated herein by reference in its entirety.

TABLE 3

Carbon dioxide separation from air and natural gas by ZIF-90 and PSM-ZIF-90s

| ZIF name | $CO_2/N_2$ selectivity[a] | $CO_2/CH_4$ selectivity[a] | Adsorption temperature (K) | Reference |
|---|---|---|---|---|
| ZIF-90 | 23.6 | 11.3 | 298 | Reproduced |
| ZIF-90 | 15 (simulated) | —[b] | 298 | Hu et al.[d] |
| ZIF-92A (10% PSM-ZIF-90) | 44.6 | 7.2 | 298 | This work |
| ZIF-92B (25% PSM-ZIF-90) | 25.1 | 7.91 | 298 | This work |
| ZIF-92C (50% PSM-ZIF-90) | 42.2 | 12.5 | 298 | This work |
| ZIF-92D (75% PSM-ZIF-90) | 77.6 | 64.6 | 298 | This work |
| ZIF-92 (100% PSM-ZIF-90) | —[c] | —[c] |  | Reproduced |

[a] Calculated from single component isotherms by Henry's law
[b] Data not available
[c] Not measurable due to detection limit for $N_2$ and $CH_4$
[d] J. Hu, Y. Liu, J. Liu and C. Gu, *Fuel*, 2017, 200, 244-251, incorporated herein by reference in its entirety.

In summary, the controlled post-synthetic modifications of ZIF-90 with amines resulted in the synthesis of new hybrid ZIF materials having 10, 25, 50, and 75% post-synthetically modified ligands. These new materials have controlled diffusion and carbon dioxide uptake compared to nitrogen and natural gas, enabling their use for $CO_2$ capture and separation.

The invention claimed is:

1. A hybrid zeolitic imidazolate framework having an isolated purity of at least 95 wt. %, which is a coordination product formed between:

zinc(II) ions;

a linker of formula (I); and a linker of formula (II);

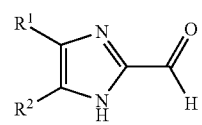
(I)

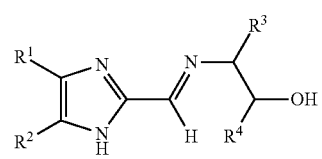
(II)

or a stereoisomer or tautomer thereof,
wherein:
each linker of formulae (I) and (II) links together adjacent zinc(II) ions,
$R^1$ and $R^2$ are independently a hydrogen, an optionally substituted alkyl, an optionally substituted aryl, a halo, a nitro, or a cyano, and
$R^3$ and $R^4$ are independently hydrogen, an optionally substituted alkyl, an optionally substituted aryl, or an optionally substituted arylalkyl.

2. The hybrid zeolitic imidazolate framework of claim 1, wherein a relative mol % of the linker of formula (II) is 10 to 75 mol %, based on a total molar amount of the linkers of formulae (I) and (II).

3. The hybrid zeolitic imidazolate framework of claim 1, wherein, each based on a total molar amount of the linkers of formulae (I) and (II):
a relative mol % of the linker of formula (II) is 10 mol %,
a relative mol % of the linker of formula (II) is 25 mol %,
a relative mol % of the linker of formula (II) is 50 mol %, or
a relative mol % of the linker of formula (II) is 75 mol %.

4. The hybrid zeolitic imidazolate framework of claim 1, wherein $R^1$ and $R^2$ are each hydrogen.

5. The hybrid zeolitic imidazolate framework of claim 1, wherein $R^3$ and $R^4$ are each hydrogen.

6. The hybrid zeolitic imidazolate framework of claim 1, wherein
the linker of formula (I) is

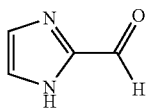

and the linker of formula (II) is

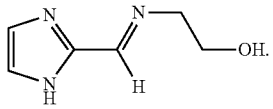

7. The hybrid zeolitic imidazolate framework of claim 1, which is isoreticular with ZIF-90.

8. The hybrid zeolitic imidazolate framework of claim 1, which has a BET surface area of 3 to 850 m²/g.

9. The hybrid zeolitic imidazolate framework of claim 1, which has a micropore volume of 0.05 to 0.25 cm³/g.

10. The hybrid zeolitic imidazolate framework of claim 1, which has a $CO_2$ uptake capacity of 20 to 95 cm³/g at 273 K and 15 to 47 cm³/g at 298 K, each at 760 Torr.

11. The hybrid zeolitic imidazolate framework of claim 1, which has an ideal selectivity of $CO_2/N_2$ of 25 to 80, and an ideal selectivity of $CO_2/CH_4$ of 5 to 65.

12. A method of making the hybrid zeolitic imidazolate framework of claim 1, the method comprising:
obtaining a parent zeolitic imidazolate framework formed from coordination between zinc(II) ions and the linker of formula (I);
post-synthetically modifying the parent zeolitic imidazolate framework by reacting a portion of a total number of aldehyde groups present in the parent zeolitic imidazolate framework from the linker of formula (I) with an amino alcohol of formula (III)

$$H_2N\text{---}CH(R^3)\text{---}CH(R^4)\text{---}OH \quad \text{(III)}$$

in an alcoholic solvent to form the hybrid zeolitic imidazolate framework in a reaction mixture; and
isolating the hybrid zeolitic imidazolate framework from the reaction mixture by filtering, washing with an alcohol, and drying at 80 to 120° C.

13. The method of claim 12, wherein the parent zeolitic imidazolate framework is post-synthetically modified with a molar ratio of the amino alcohol of formula (III) to the parent zeolitic imidazolate framework of 0.2:1 to 1.6:1, which provides a relative mol % of the linker of formula (II) of 10 to 75 mol %, based on a total molar amount of the linkers of formulae (I) and (II).

14. The method of claim 12, wherein the amino alcohol of formula (III) is ethanolamine and the linker of formula (I) is

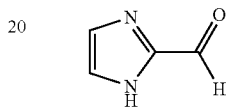

and the linker of formula (II) is

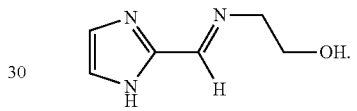

15. A method of capturing $CO_2$ from a gas mixture, the method comprising:
contacting the gas mixture with the hybrid zeolitic imidazolate framework of claim 1 to adsorb at least a portion of the $CO_2$ into the hybrid zeolitic imidazolate framework, thereby forming a loaded hybrid zeolitic imidazolate framework and a gas stream depleted in $CO_2$ compared to the gas mixture.

16. The method of claim 15, wherein the gas mixture further comprises at least one other gas selected from the group consisting of hydrogen, oxygen, nitrogen, methane, and carbon monoxide.

17. The method of claim 15, wherein the gas mixture is a pre-combustion gas mixture comprising 15 to 50 vol. % of $CO_2$, based on a total volume of the gas mixture.

18. The method of claim 15, wherein the gas mixture is a post-combustion gas mixture comprising 5 to 15 vol. % of $CO_2$, based on a total volume of the gas mixture.

19. The method of claim 15, wherein the gas mixture has a temperature of −5 to 50° C.

20. The method of claim 15, wherein the gas stream depleted in $CO_2$ contains at least 25% less $CO_2$ by volume compared to a volume of $CO_2$ present in the gas mixture.

* * * * *